United States Patent [19]
Daneshtalab et al.

[11] Patent Number: 6,153,616
[45] Date of Patent: Nov. 28, 2000

[54] TRIAZOLES AS THERAPEUTIC AGENTS FOR FUNGAL INFECTIONS

[75] Inventors: Mohsen Daneshtalab; Yadagiri Bathini; Dai Nguyen; Inderjit Sidhu; Mark Abel; Chan Ha, all of Edmonton; Sameeh Salama, Sherwood Park; Jehangir Khan, Edmonton; Ronald Micetich, Sherwood Park, all of Canada; Tetsuo Furukawa; Norio Unemi, both of Tokushima, Japan

[73] Assignees: Synphar Laboratories, Inc., Alberta, Canada; Taiho Pharmaceuticals Co., Ltd., Tokyo, Japan

[21] Appl. No.: 09/008,577

[22] Filed: Jan. 16, 1998

Related U.S. Application Data
[60] Provisional application No. 60/084,187, Jan. 17, 1997.

[51] Int. Cl.$^7$ ..................... A61K 31/496; C07D 403/10; C07D 403/14
[52] U.S. Cl. ................ 514/254.02; 514/254.05; 514/254.07; 544/366; 544/369
[58] Field of Search .................. 544/366, 369; 514/252, 254.02, 254.05, 254.07

[56] References Cited

U.S. PATENT DOCUMENTS

| | | | |
|---|---|---|---|
| 4,503,063 | 3/1985 | Richardson et al. | 514/383 |
| 4,738,962 | 4/1988 | Holmwood et al. | 514/252 |
| 4,885,294 | 12/1989 | Ray et al. | 514/227.8 |
| 5,047,548 | 9/1991 | Richardson et al. | 548/267.6 |
| 5,545,652 | 8/1996 | Itoh et al. | 514/383 |

FOREIGN PATENT DOCUMENTS 0 321 131  12/1988  European Pat. Off. .

OTHER PUBLICATIONS

Tasaka et al.; "Optically Active Antifungal Azoles. I. Synthesis and Antifungal Activity of (2R,3R)-2-(2,4-Difluorophenyl)-3-mercapto-1-(1H-1,2,4-triazol-1-yl)-2-butanol and Its Stereoisomers"; Jun. 1993; Chem. Pharm. Bull. 41(6) 1035-1042 (1993).
Naito et al.; ER-30346 "Triazole Antifungal"; Drugs of the Future 1996, 21(1):20-24.
Fromtling et al.; SCH 51048 "Antifungal"; Drugs of the Future 1995, 20(3): 241-247.
Fromtling et al.; SCH-56532 "Antifungal"; Drugs of the Future 1996, 21(2): 160-166.
Fromtling et al.; UK-109496 "Voriconazole"; "Antifungal"; Drugs of the Future 1996, 21(3): 266-271.
Itoh et al.; "TAK-187, a New Antifungal Triazole: Synthesis and Antifungal Activity"; 36th ICAAC, Sep. 15-18, 1996, New Orleans, Louisiana.
Heeres et al.; "Antimycotic Azoles. 7. Synthesis and Antifungal Properties of a Series of Novel Triazol-3-ones"; J. Med. Chem. 1984, 27, 894-900.
Saksena et al; "SCH 51048, A Novel Broad-Spectrum Orally Active Antifungal Agent: Synthesis and Preliminary Structure-Activity Profile"; Bioorganic & Medicinal Chemistry Letters, vol. 5, No. 2, pp. 127-132, 1995.
Ogura et al.; Abstract; "KP-103, a Novel Topical Antifungal Triazole: Structure-Activity Relationships of Azolylamine Derivatives"; 36th Interscience Conference on Antimicrobial Agents and Chemotherapy, New Orleans, Louisiana; Poster session: Sep. 15-18, 1996.
"Solution Phase Combinatorial Synthesis of Arylpiperazines", Neuville, et al.; Tetrahedron Letters, vol. 38. No. 23, pp. 4091-4094, 1997.
Zhang et al, Chemical Abstracts, vol. 119, No. 139186 (1993).

*Primary Examiner*—Emily Bernhardt
*Attorney, Agent, or Firm*—Arent Fox Kintner Plotkin Kahn

[57] ABSTRACT

A compound of formula I, or an optical isomer or pharmaceutically acceptable salt thereof,

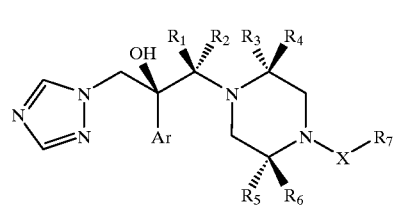

is disclosed as well as a pharmaceutical composition and a method of treating or preventing a fungal infection using the compound.

28 Claims, No Drawings

TRIAZOLES AS THERAPEUTIC AGENTS FOR FUNGAL INFECTIONS

CROSS REFERENCE TO RELATED APPICATION

This application claims the benefit of U.S. Provisional Application Ser. No. 60/084,187, filed Jan. 17, 1997, in the names of the same inventors and bearing the same title.

FIELD OF THE INVENTION

The present invention relates to the processes for the preparation of triazole compounds of formula I, i.e. 2-aryl-3-(4-substituted piperazin-1-yl)-1-(1H-1,2,4-triazol-1-yl) butan-2-ols, and their use in treating and or preventing the fungal infections in mammals preferably in humans.

BACKGROUND OF THE INVENTION

Recently the incidence of serious fungal infection has become very prominent in patients undergoing chemotherapy for cancer, organ transplants and patients with AIDS. Most of these infections are caused by opportunistic pathogens like Candida spp., Aspergillus spp., *Pneumocystis camii* and *Cryptococcus neoformans*. The antifungal agents available in the market suffer with draw backs such as, toxicity, narrow spectrum of activity, fungistatic profile rather fungicidal. Some of them also exhibit drug-drug interactions and, as a result, therapy becomes very complex. In view of the high incidence of fungal infections in immunocompromised patients and the recent trend for the steady increase of the populations of these patients, demands for new antifungal agents with broad spectrum of activity and good pharmacokinetic properties have increased.

Within the available drugs to treat fungal infections, the azole class appears to be more promising. This class of compounds inhibit the biosynthesis of ergosterol in fungi, which is the main constituent of fungal cell membrane. Fluconazole and itraconazole are routinely used for maintenance of fungal infections. Although fluconazole is highly bioavailable, it is not active against filamentous fungi and emergence of fungal resistance has been reported recently (Antimicrob. Agents Chemother. 1995, 39, 1–8). Itraconazole is active against filamentous fungi, but it shows inconsistent results, maybe due to its high protein binding properties and less bioavailability. During the last few years, several research groups have been actively searching for new azoles with optimum pharmacokinetic properties. As a result, a number of candidate azoles have emerged, and some of them are undergoing preclinical and clinical evaluation. Some of the candidate azoles are disclosed in the following publications:

Sch 51048 (Drugs of the Future, 1995, 20, 241–247).
Sch 56592; Antimicrob. Agents Chemother. (1996, 40, 1910–1913; 36th Interscience Conference Antimicrob. Agents Chemother. September 1996, New Orleans, Abst. F87–F102).
UK-109, 496 (Drugs of the Future, 1996, 21, 266–271; EP 440372).
TAK-187; 36th Interscience Conference Antimicrob. Agents Chemother. September 1996, New Orleans, Abst. F74; EP 567982).
KP-103 (36th Interscience Conference Antimicrob. Agents Chemother. September 1996, New Orleans, Abst. F78, WO 94126734).
ER-30346 (Drugs of the Future, 1996, 21, 20–24)

In the present invention, we report new triazoles with broad spectrum anti-fungal activity. The triazoles are particularly effective against systemic and lung invasive fungal infections.

SUMMARY OF THE INVENTION

The present invention relates to new triazole derivatives which can be utilised to treat or prevent fungal infections in animals, preferably in humans.

In accordance to the present invention, there is provided an antifungal triazole of the general formula I, i.e. 2-aryl-3-(4-substituted piperazin-1-yl)-1-(1H-1,2,4-triazol-1-yl)-2-ols and pharmaceutically acceptable salts thereof,

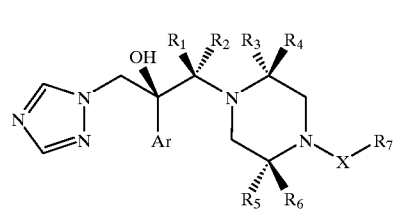

wherein:
Ar is a phenyl group which is unsubstituted or substituted by 1–3 substituents each independently selected from the group consisting of halogen, $CF_3$ and $OCF_3$;
$R_1$ and $R_2$ are each independently hydrogen or $C_1$–$C_4$ alkyl group which is unsubstituted or substituted by 1–3 substituents each independently selected from the group consisting of halogen, hydroxy, $C_1$–$C_4$ alkoxy and amino, with the proviso that where $R_1$ is hydrogen, $R_2$ is other than hydrogen, and vice versa;
$R_3$ and $R_4$ are each independently hydrogen or $C_1$–$C_4$ alkyl group which is unsubstituted or substituted by 1–3 substituents each independently selected from the group consisting of halogen, hydroxy, $C_1$–$C_4$ alkoxy and amino, or $R_3$ and $R_4$ together form =S;
$R_5$ and $R_6$ are each independenly hydrogen or $C_1$–$C_4$ alkyl group which is unsubstituted or substituted by 1–3 substituents each independently selected from the group consisting of halogen, hydroxy, $C_1$–$C_4$ alkoxy and amino, or $R_5$ and $R_6$ together form =S;
X is selected from the group consisting of a direct bond, CO, CS, $SO_2$ and —N=N—;
$R_7$ is selected from the group consisting of
  i) hydrogen,
  ii) CN
  iii) CHO
  iv) phenyl which is unsubstituted or substituted with 1–3 substituents each independently selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino, (2) $C_1$–$C_4$ alkoxy, (3) halogen, (4) formyl, (5) carboxyl, (6) $C_1$–$C_4$ acyloxy, (7) $C_1$–$C_4$ alkoxycarbonylamino, (8) phenyl- or naphthyl-oxycarbonylamino, (9) semicarbazido, (10) formamido, (11) thioformamido, (12) hydroxy, (13) nitro, (14) amino, (15) furyl, (16) triazolyl, (17) thienyl, (18) oxazolyl, (19) imidazolyl and (20) triazolone-yl,
  v) a 5- or 6-membered monocyclic or 8- to 10-membered bicyclic heterocycle having 1–4 heteroatoms each independently selected from the group consisting of N, O and S, which heterocycle is unsubstituted or ring-substituted with 1–3 substituents each independently selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino, (2) benzyl which is unsubstituted or substituted with 1–3 substituents selected from the group consisting of $C_1$–$C_4$ alkyl, $CF_3$, halogen and $OCF_3$, (3) halogen, (4) hydroxy, (5) nitro, (6) amino, (7) $C_1$–$C_4$ acylamino, (8) formyl, (9) formamido, (10) thioformamido, (11) $C_1$–$C_4$ alkoxycarbonylamino, (12) phenyl- or naphthyl-oxycarbonylamino and (13) semicarbazido, vi) $NHR_8$ wherein $R_8$ is selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino, (2) phenyl which is unsubstituted or substituted with 1–3 substituents each independently selected from the group consisting of (a) $C_1$–$C_4$ alkyl which is unsubstituted or substituted with 1–3 substituents each independently selected from the group consisting of halogen, hydroxy, $C_1$–$C_4$ alkoxy and amino, (b) $C_1$–$C_4$ alkoxy, (c) halogen, (d) formyl, (e) carboxyl, (f) $C_1$–$C_4$ acyloxy, (g) $C_1$–$C_4$ alkoxycarbonylamino, (h) phenyl- or naphthyl-oxycarbonylamino, (i) semicarbazido, (j) formamido, (k) thioformamido, (l) hydroxy, (m) nitro, (n) amino, (o) furyl, (p) triazolyl, (q) thienyl, (r) oxazolyl, (s) imidazolyl and (t) triazolone-yl, and (3) a 5- or 6-membered monocyclic or 8- to 10-membered bicyclic heterocycle having 1–3 heteroatoms each independently selected from the group consisting of N, O and S, which is unsubstituted or substituted with 1–3 substituents each independently selected from the group consisting of hydroxy, halogen, amino and carboxyl, vii) $OR_9$ wherein $R_9$ is selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino, (2) phenyl which is unsubstituted or substituted with 1–3 substituents each independently selected from the group consisting of (a) $C_1$–$C_4$ alkyl which is unsubstituted or substituted with 1–3 substituents each independently selected from the group consisting of halogen, hydroxy, $C_1$–$C_4$ alkoxy and amino, (b) $C_1$–$C_4$ alkoxy, (c) halogen, (d) formyl, (e) carboxyl, (f) $C_1$–$C_4$ acyloxy, (9) $C_1$–$C_4$ alkoxycarbonylamino, (h) phenyl- or naphthyl-oxycarbonylamino, (i) semicarbazido, (j) formamido, (k) thioformamido, (l) hydroxy, (m) nitro, (n) amino, (o) furyl, (p) triazolyl, (q) thienyl, (r) oxazolyl, (s) imidazolyl and (t) triazolone-yl and (3) a 5- or 6-membered monocyclic or 8- to 10-membered bicyclic heterocycle having 1–3 heteroatoms each independently selected from the group consisting of N, O and S, which is unsubstituted or substituted with 1–3 substituents each independently selected from the group consisting of (a) $C_1$–$C_4$ alkyl which is unsubstituted or substituted with 1–3 substituents each independently selected from the group consisting of halogen, hydroxy, $C_1$–$C_4$ alkoxy and amino, (b) phenyl which is unsubstituted or substituted with 1–3 substituents each independently selected from the group consisting of (A) $C_1$–$C_4$ alkyl which is unsubstituted or substituted with 1–3 substituents each independently selected from the group consisting of halogen, hydroxy, $C_1$–$C_4$ alkoxy and amino, (B) $C_1$–$C_4$ alkoxy, (C) halogen, (D) formyl, (E) carboxyl, (F) $C_1$–$C_4$ acyloxy, (G) $C_1$–$C_4$ alkoxycarbonylamino, (H) phenyl- or naphthyl-oxycarbonylamino, (I) semicarbazido, (J) formamido, (K) thioformamido, (L) hydroxy, (M) nitro, (N) amino, (O) furyl, (P) triazolyl, (Q) thienyl, (R) oxazolyl, (S) imidazolyl and (T) triazolone-yl, (c) naphthyl which is unsubstituted or substituted with 1–3 substituents each independently selected from the group consisting of (A) $C_1$–$C_4$ alkyl which is unsubstituted or substituted with 1–3 substituents each independently selected from the group consisting of halogen, hydroxy, $C_1$–$C_4$ alkoxy and amino, (B) $C_1$–$C_4$ alkoxy, (C) halogen, (D) formyl, (E) carboxyl, (F) $C_1$–$C_4$ acyloxy, (G) $C_1$–$C_4$ alkoxycarbonylamino, (H) phenyl- or naphthyl-oxycarbonylamino, (I) semicarbazido, (J) formamido, (K) thioformamido, (L) hydroxy, (M) nitro, (N) amino, (O) furyl, (P) triazolyl, (Q) thienyl, (R) oxazolyl, (S) imidazolyl and (T) triazolone-yl, (d) a 5- or 6-membered monocyclic or 8- to 10-membered bicyclic heterocycle having 1–3 heteroatoms each independently selected from the group consisting of N, O and S, (e) ($C_1$–$C_4$ alkyl)phenyl, (f) ($C_1$–$C_4$ alkyl)naphthyl, (g) hydroxy, (h) halogen, (i) amino and (j) carboxyl, and viii) a group of the formula

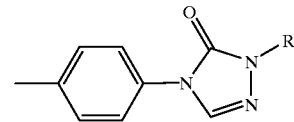

wherein R is selected from the group consisting of (1) hydrogen, (2) $C_1$–$C_{10}$ alkyl which is unsubstituted or substituted by 1–5 substituents each independently selected from the group consisting of halogen, hydroxy, $C_1$–$C_4$ alkoxy and amino, (3) phenyl which is unsubstituted or substituted with 1–3 substituents each independently selected from the group consisting of (a) $C_1$–$C_4$ alkyl which is unsubstituted or substituted with 1–3 substituents each independently selected from the group consisting of halogen, hydroxy, $C_1$–$C_4$ alkoxy and amino, (b) $C_1$–$C_4$ alkoxy, (c) halogen, (d) formyl, (e) carboxyl, (f) $C_1$–$C_4$ acyloxy, (g) $C_1$–$C_4$ alkoxycarbonylamino, (h) phenyl- or naphthyl-oxycarbonylamino, (i) semicarbazido, (j) formamido, (k) thioformamido, (l) hydroxy, (m) nitro, (n) amino, (o) furyl, (p) triazolyl, (q) thienyl, (r) oxazolyl, (s) imidazolyl, (t) trizolone-yl, (u) $CF_3$ and (v) $OCF_3$, (4) a 5- or 6-membered monocyclic or 8- to 10-membered bicyclic heterocycle having 1–3 heteroatoms each independently selected from the group consisting of N, O and S, which is unsubstituted or substituted with 1–3 substituents each independently selected from the group consisting of (a) $C_1$–$C_4$ alkyl which is unsubstituted or substituted with 1–3 substituents each independently selected from the group consisting of halogen, hydroxy, $C_1$–$C_4$ alkoxy and amino, (b) phenyl which is unsubstituted or substituted with 1–3 substituents each independently selected from the group consisting of (A) $C_1$–$C_4$ alkyl which is unsubstituted or substituted with 1–3 substituents each independently selected from the group consisting of halogen, hydroxy, $C_1$–$C_4$ alkoxy and amino, (B) $C_1$–$C_4$ alkoxy, (C) halogen, (D) formyl, (E) carboxyl, (F) $C_1$–$C_4$ acyloxy, (G) $C_1$–$C_4$ alkoxycarbonylamino, (H) phenyl- or naphthyl-oxycarbonylamino, (I) semicarbazido, (J) formamido, (K) thioformamido, (L) hydroxy, (M) nitro, (N) amino, (O) furyl, (P) triazolyl, (Q) thienyl, (R) oxazolyl, (S) imidazolyl and (T) triazolone-yl, (c) naphthyl which is unsubstituted or substituted with 1–3 substituents each independently selected from the group consisting of (A) $C_1$–$C_4$ alkyl which is unsubstituted or substituted with 1–3 substituents each independently selected from the group consisting of halogen, hydroxy, $C_1$–$C_4$ alkoxy and amino, (B) $C_1$–$C_4$ alkoxy, (C) halogen, (D) formyl, (E) carboxyl, (F) $C_1$–$C_4$ acyloxy, (G) $C_1$–$C_4$ alkoxycarbonylamino, (H) phenyl- or naphthyl-oxycarbonylamino, (I) semicarbazido, (J) formamido, (K) thioformamido, (L) hydroxy, (M) nitro, (N) amino, (O) furyl, (P) triazolyl, (Q) thienyl, (R) oxazolyl, (S) imidazolyl and (T) triazolone-yl, (d) a 5- or 6-membered monocyclic or 8- to 10-membered bicyclic heterocycle having 1–3 heteroatoms each independently selected from the group consisting of N, O and S, (e) ($C_1$–$C_4$ alkyl)phenyl, (f) ($C_1$–$C_4$ alkyl)naphthyl, (g) hydroxy, (h) halogen, (i) amino and (j) carboxyl, (5) phenyl($C_1$–$C_4$ alkyl) which is unsubstituted or ring-substituted with 1–3 substituents each independently selected from the group consisting of (a) $C_1$–$C_5$ alkyl which is unsubstituted or substituted with 1–3 substituents each independently selected from the group consisting of halogen, hydroxy, $C_1$–$C_4$ alkoxy and amino, (b) halogen, (c) halo($C_1$–$C_4$ alkyl), (d) $C_1$–$C_4$ alkoxy, (e) hydroxy, (f) amino, (g) carboxyl, (h) trifluormethoxyl, (i) trifluoromethyl, (j) tetrafluoroethyl, (k) tetrafluoroethoxyl, (l) tetrafluoropropyl and (m) tetrafluoropropoxyl, (6) naphthyl($C_1$–$C_4$ alkyl) which may be substituted with 1–6 substituents selected from (a) $C_1$–$C_5$ alkyl which is unsubstituted or substituted with 1–3 substituents each independently selected from the group consisting of halogen, hydroxy, $C_1$–$C_4$ alkoxy and amino, (b) halogen, (c) ($C_1$–$C_4$ alkyl) halo, (d) $C_1$–$C_4$ alkoxy, (e) hydroxy, (f) amino, (g) carboxyl, (h) trifluormethoxyl, (i) trifluoromethyl, (j) tetrafluoroethyl, (k) tetrafluoroethoxyl, (l) tetrafluoropropyl and (m) tetrafluoropropoxyl, (7) methoxyl, (8) trifluormethoxyl, (9) trifluoromethyl, (10) trifluoroethyl, (11) tetrafluoroethyl, (12) tetrafluoroethoxyl, (13) tetrafluoropropyl and (14) tetrafluoropropoxyl.

DESCRIPTION OF THE PREFERRED EMBODIMENTS

In the above definition of formula I, halogen is fluorine, chlorine, bromine or iodine. Preferred halogens are fluorine and chlorine.

$C_1$–$C_4$ alkyl is, for example, methyl, ethyl, propyl, 1-methylethyl, n-butyl, 1-methylethyl, isopropyl, 1,1-dimethylethyl, 1-methylpropyl, 2-methylpropyl, cyclopropyl and cyclobutyl. Preferred alkyls are methyl and ethyl.

Examples of Ar groups include, 4-fluorophenyl, 2-4-difluorophenyl, 2,4,6-trifluorophenyl, 4-chlorophenyl, 2,4-dichlorophenyl, 2,4,6-trichlorophenyl, 4-trifluoromethylphenyl and 4-trifluoromethoxyphenyl. Preferred Ar groups are phenyl group having 1 or 2 substituents each independently selected from fluorine, chlorine, trifluoromethyl and trifluromethoxy. Most preferably, Ar is 2,4-difluorophenyl, 2,4-dichlorophenyl, 4-trifluromethylphenyl or 4-trifluoromethoxyphenyl.

Examples of 5-or 6-membered monocyclic rings are 1-pyrrolyl, 2-pyrrolyl, 3-pyrrolyl, 2-furyl, 3-furyl, 2-thienyl, 3-thienyl, 1-imidazolyl, 4-imidazolyl, 1-pyrazolyl, 3-pyrazolyl, 4-pyrazolyl, 5-pyrazolyl, 1-(1H)-1,2,4-triazolyl, 3-(1H)-1,2,4-triazolyl, 3-(4H)-1,2,4-triazolyl, 5-(1H)-1,2,4-triazolyl, 4-(4H)-1,2,4-triazolyl, 1,2,3-triazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4 -thiadiazol-2-yl, 5-(1H)-tetrazolyl, 5-(2H)-tetrazolyl, 2-pyridyl, 3-pyridyl, 4-pyridyl, 2-pyrimidyl, 4-pyrimidyl and 5-pyrimidyl.

Examples of 8- to 10-membered bicyclic heterocycle groups are 2-benzimidazolyl, 5-benzimidazolyl, 2-benzoxazolyl, 5-benzoxazolyl, 6-benzoxazolyl, 2-benzothiazolyl, 5-benzothiazolyl, 6-benzothiazolyl, imidazolo[4,5-b]pyridin-2-yl, imidazolo[4,5-b]pyridin-5-yl, oxazolo[5,4-b]pyridin-2-yl, oxazolo[5,4-b]pyridin-5-yl, oxazolo[5,4-b]pyridin-6-yl, thiazolo[5,4-b]pyridin-2-yl, thiazolo[5,4-b]pyridin-5-yl and thiazolo[5,4-b]pyridin-6-yl.

Triazolone-yl may be 2- or 5-substutitued 1,2,4-triazol-3-one, such as 2H-1,2,4-triazol-3-one-4-yl or 4H-1,2,4-triazol-3-one-2-yl.

Examples of $R_1$ include hydrogen, methyl, ethyl, propyl, hydroxymethyl, alkoxymethyl, fluoromethyl and trifluoromethyl. Preferably, $R_1$ is alkyl. Most preferably, $R_1$ is methyl.

Examples of $R_2$ include hydrogen, methyl, ethyl, propyl, hydroxymethyl, alkoxymethyl, fluromethyl and trifluoromethyl. Preferably, $R_2$ is hydrogen.

Depending on the substituents in formula I, the compound may have one or more than one asymmetric centers, resulting in possible stereoisomers. This invention relates to single individual isomers as well as mixture of isomers.

When $R_1$ and $R_2$ are the same, formula I has one asymmetric center and there are two possible isomers, i.e. 2R and 2S isomers. This invention relates to mixtures as well as individual isomers. The most preferable isomer is the 2R isomer.

When $R_1$ and $R_2$ are different, formula I has two asymmetric centers, and there are four possible isomers, i.e. 2R,3R; 2R,3S; 2S, 3R and 2S,3S. This invention relates to the mixture of isomers as well as individual isomers. The most preferred isomer in this situation is 2R,3R.

It is more preferred that $R_7$ is a group

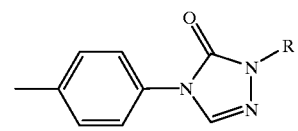

wherein R is as described above, and most preferred that the other groups additionally are as follows: Ar is 2,4-difluorophenyl, $R_1$ is methyl, and $R_2$ through $R_6$ are each hydrogen.

Specifically, the more preferred embodiments of the present invention include the compounds that are disclosed in Table 3. Those disclosed in Example Nos. 36–51 are more preferred, with Example Nos. 43, 47, 50 and 51 being the most preferred.

The compounds of formula I can be prepared by a convergent approach from the epoxide of formula II and the piperazino compound of formula III (see Scheme 1). The epoxides were prepared following the synthetic routes described in the literature (Chem. Pharm. Bull., 1993, 41, 1035–1042).

The synthetic routes for the preparation of certain piperazino compounds of the formula III are disclosed in Schemes 4–6 and 8. The Scheme 7 describes a linear synthetic route for preparing certain compounds of formula I. The epoxide of formula II and the piperazino compound of formula III were reacted in the presence of base such as sodium carbonate, potassium carbonate, cesium carbonate and the like. This reaction was also performed in the presence of lithium perchlorate and sodium perchlorate. The suitable solvents were chosen from acetonitrile, DMF, DMSO, THF, dichloromethane, chloroform, methanol, ethanol, isopropanol and tert-butanol. The most preferred solvents were DMF and acetonitrile. The temperature of the reaction varied from 60–180° C., depending on the solvent and reactants. The most preferred temperature was 80–140° C. The reactants were allowed to react to the completion or near to the completion of the reaction. The length of reaction time varied from few hours to several hours depending on the reactants, temperature, and the solvent.

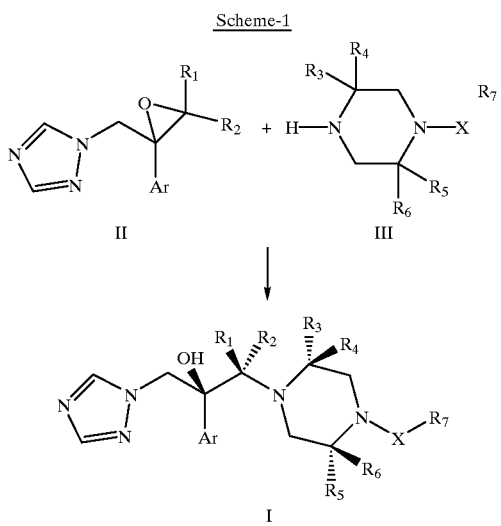

Certain compounds of formula I were prepared from a common intermediate, which forms Example 2 of this invention as described in Scheme 3. Example 2 was prepared from epoxide IV by two synthetic routes as depicted in Scheme 2. In the first route, a 1:1 molar ratio of epoxide and ethyl piperazine-1-carboxylate were reacted in the presence of potassium carbonate or lithium perchlorate in a suitable solvent. The obtained ester was hydrolysed with

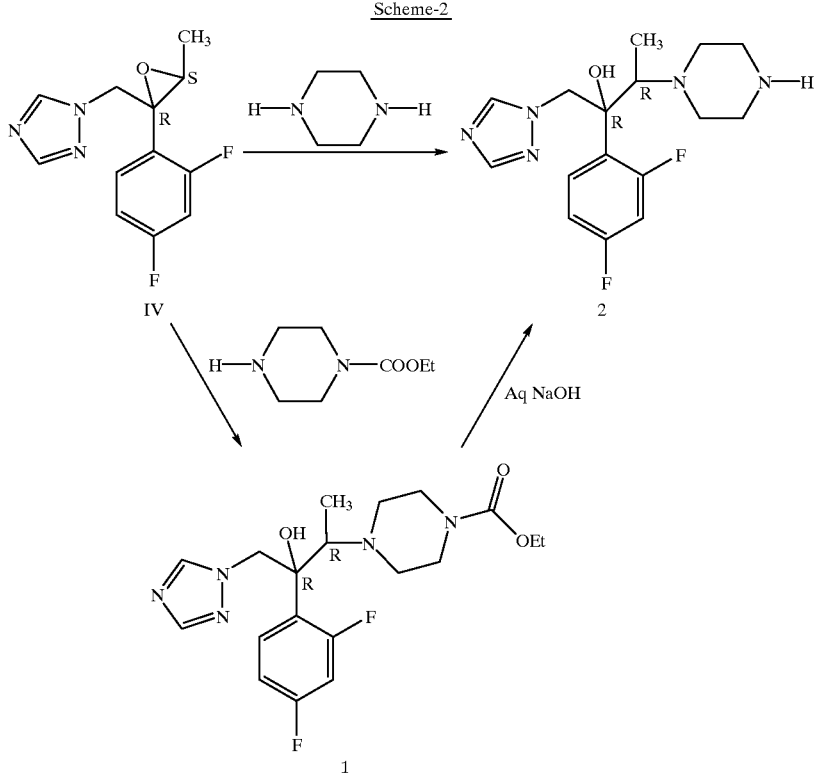

strong base such as sodium hydroxide or potassium hydroxide to give piperazinyl compound 2. In this reaction the resulting N-carboxylic acid undergoes in-situ decarboxylation to give the piperazino compound 2. In an alternate route, the piperazino compound was obtained in a single step from the reaction of epoxide IV with piperazine. In a typical procedure, the epoxide and excess piperazine were reacted in the presence of lithium perchlorate in a suitable solvent and at a desired temperature.

Certain compound of formula I wherein X is CO, $SO_2$, CS, or —N=N— were prepared as described in Scheme 3.

The compounds of formula I wherein X is CO were produced from the reaction of piperazinyl compound 2 with acid chloride ($R_7COCl$) in the presence of a base such as triethylamine, N-methylmorpholine, N,N-diisopropylethylamine. The reaction was carried out in an inert solvent at $-20°$ C. to $80°$ C. The most preferred solvents were dichloromethane, chloroform, tetrahydrofuran and acetonitrile. Most preferably the reaction was carried out at $0-25°$ C. Certain compounds of formula I wherein X is $SO_2$ were prepared from the reaction of 2 and $R_7$—$SO_2$—Cl. In these reactions, $R_7$ is as described above.

Certain compounds of formula I wherein X is CO or CS and $R_7$ is OR were prepared from the reaction of piperazinyl compound 2 and isocyanates and isothiocyanates. In a typical reaction, a 1:1 molar ratio of compound and isocyanate or isothiocyanate were reacted in a suitable solvent at $-15$ to $45°$ C. The preferred solvents were acetonitrile, ethyl acetate and dichloromethane. The preferred temperature was 0 to $25°$ C. The reaction time varied from few hours to several hours depending on the reactants, solvent and temperature.

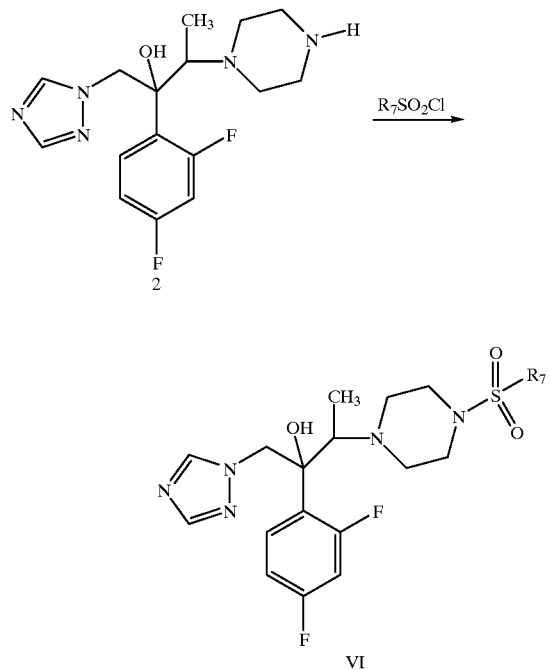

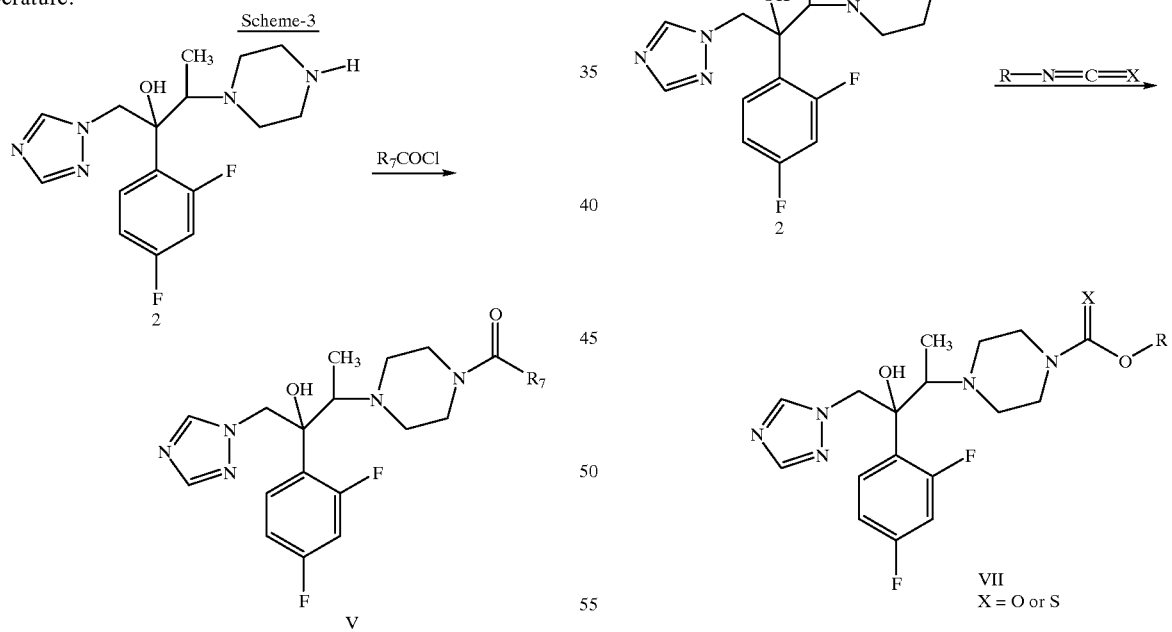

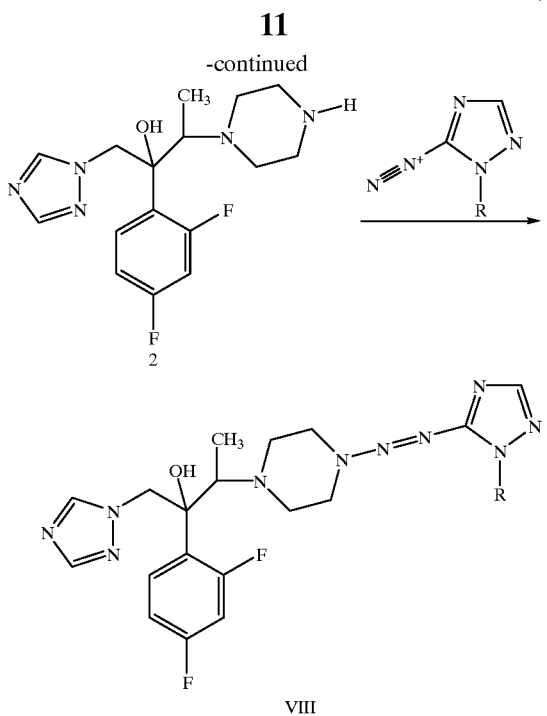

The reaction of 1H or 2H-1,2,4-triazol-3-diazonium salt with the piperazinyl compound 2 gave the N-azo compound of formula VIII. This reaction was conducted at suitable temperature in suitable solvent in the presence of base like sodium hydroxide, potassium hydroxide and potassium carbonate.

Certain compounds of formula I wherein X is bond and $R_7$ is unsubstituted or substituted azole were prepared according to Scheme 1 The synthetic routes followed for the preparation of piperazinyl azoles X, XI, XII, XIII and XVI are described in Schemes 4–6. In a typical procedure, piperazinyl azole and epoxide were heated in a suitable solvent in the presence of lithium perchlorate or potassium carbonate for 24–48 h. The molar ratio of the reactants varied from 1:1 to 1:5. After usual workup the product was purified by column chromatography.

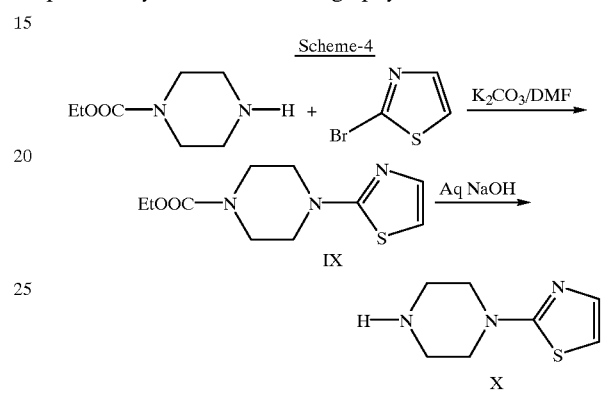

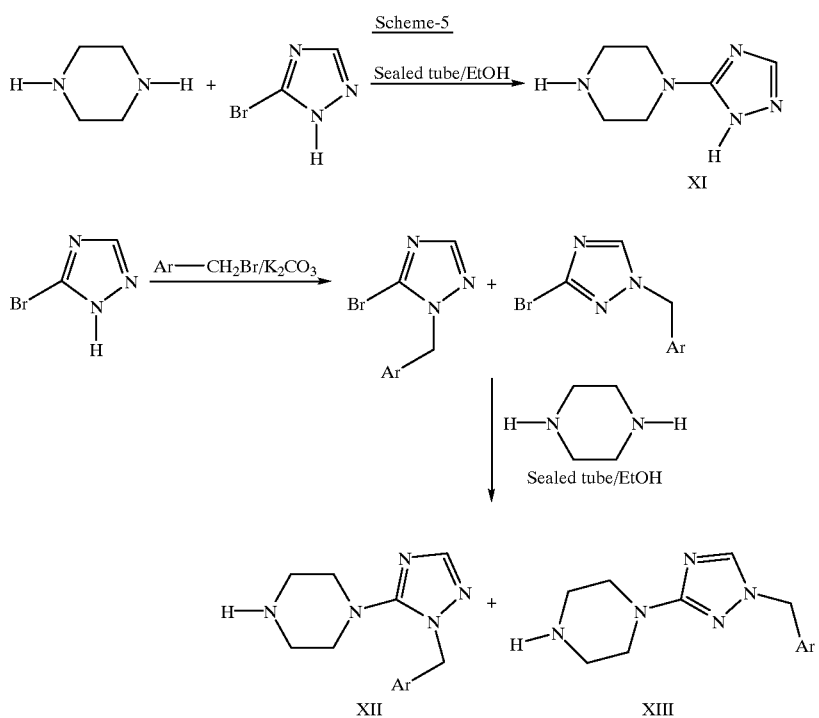

Scheme-6

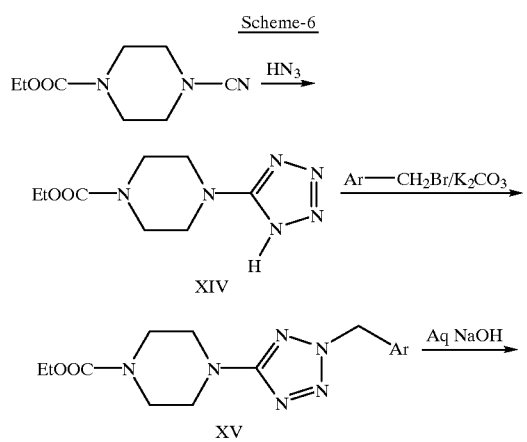

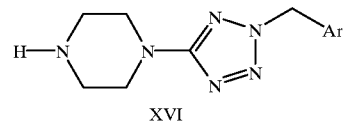

Certain compounds of formula I wherein X is a bond and $R_7$ is a 4-[2-substituted-1,2,4-triazol-3-one-4-yl]phenyl group were prepared in two independent synthetic routes. The first route involves the linear approach as described in Scheme 7. The intermediates formed during this synthesis are compounds of formula I, wherein X is bond and $R_7$ is phenyl group with substitution.

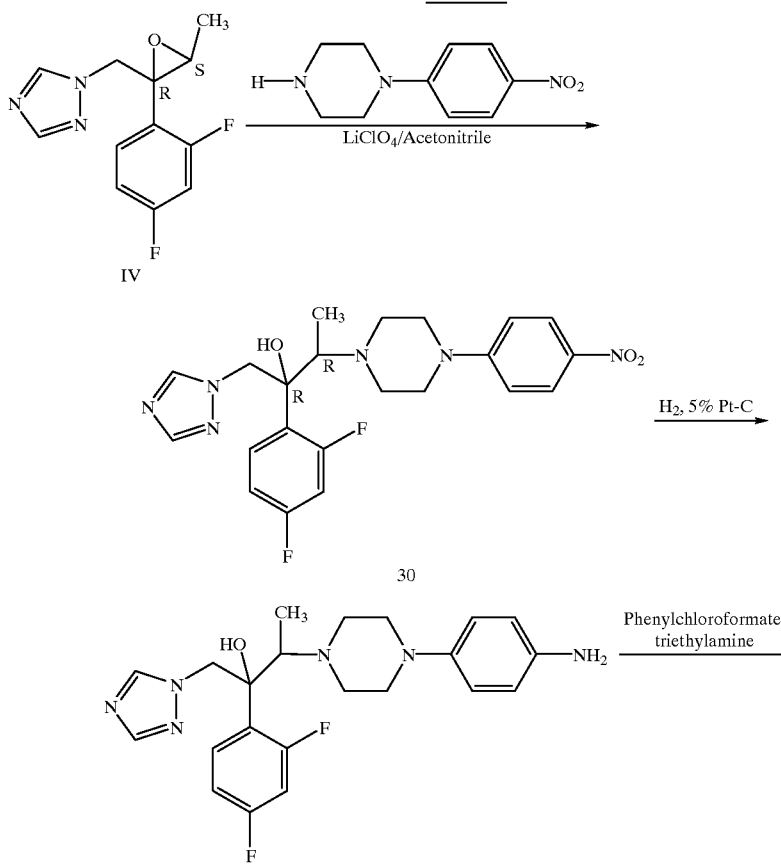

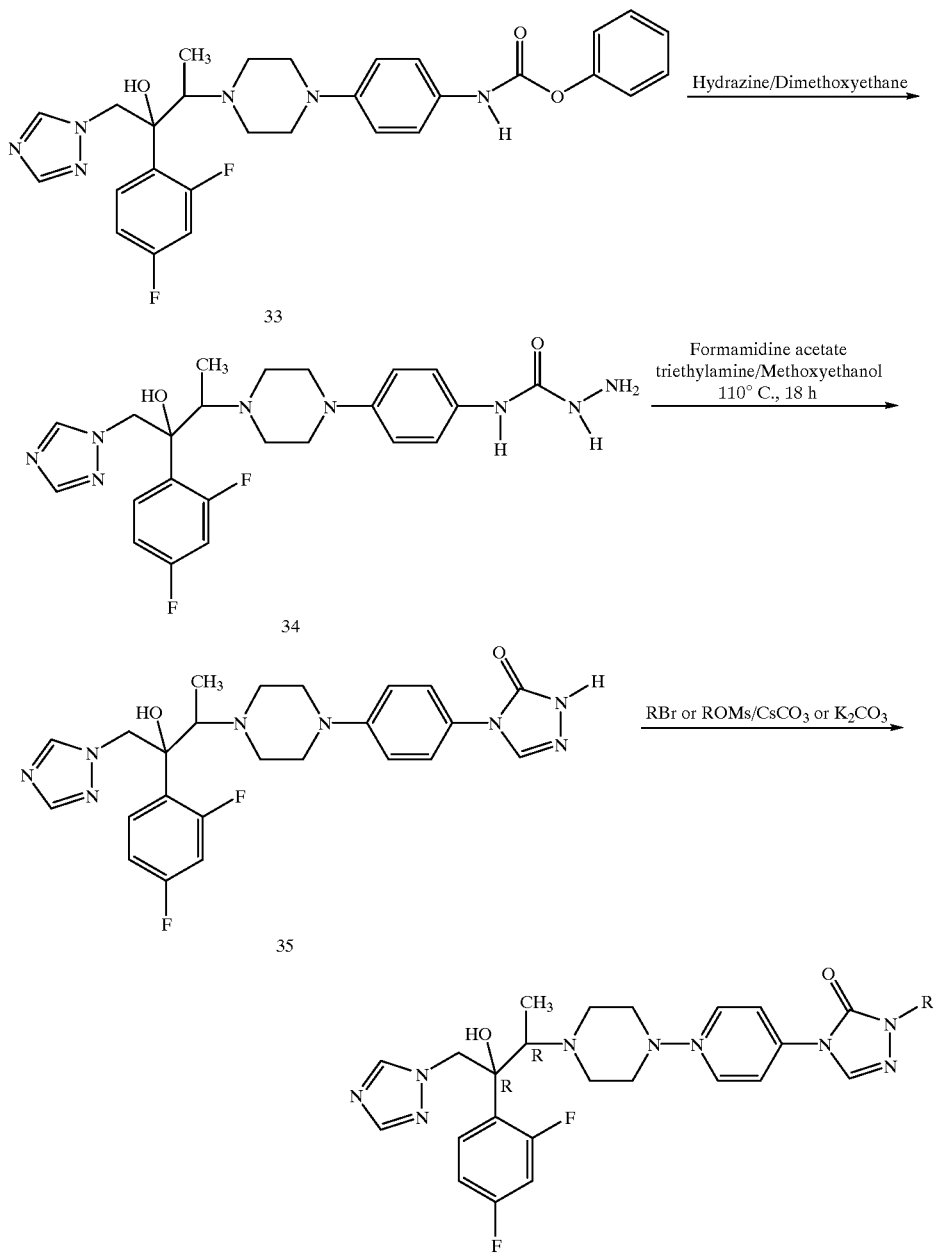

The second synthetic route involves a more efficient convergent approach (Scheme 1). In a typical procedure, an appropriate epoxide of formula II and an appropriate piperazinyl derivative XXIII were reacted in the presence of lithium perchlorate in a suitable solvent and at a suitable temperature. The reactants were allowed to react to the completion of the reaction. The reaction time varied from few hours to several hours depending on the reactants. The epoxides used in this invention are known and were prepared by following the reported procedures. The piperazino compounds of formula XXIII were prepared as described in Scheme 8.

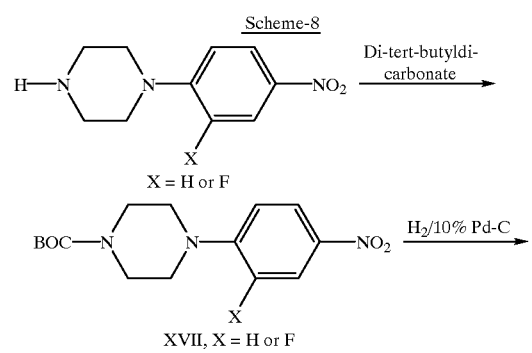

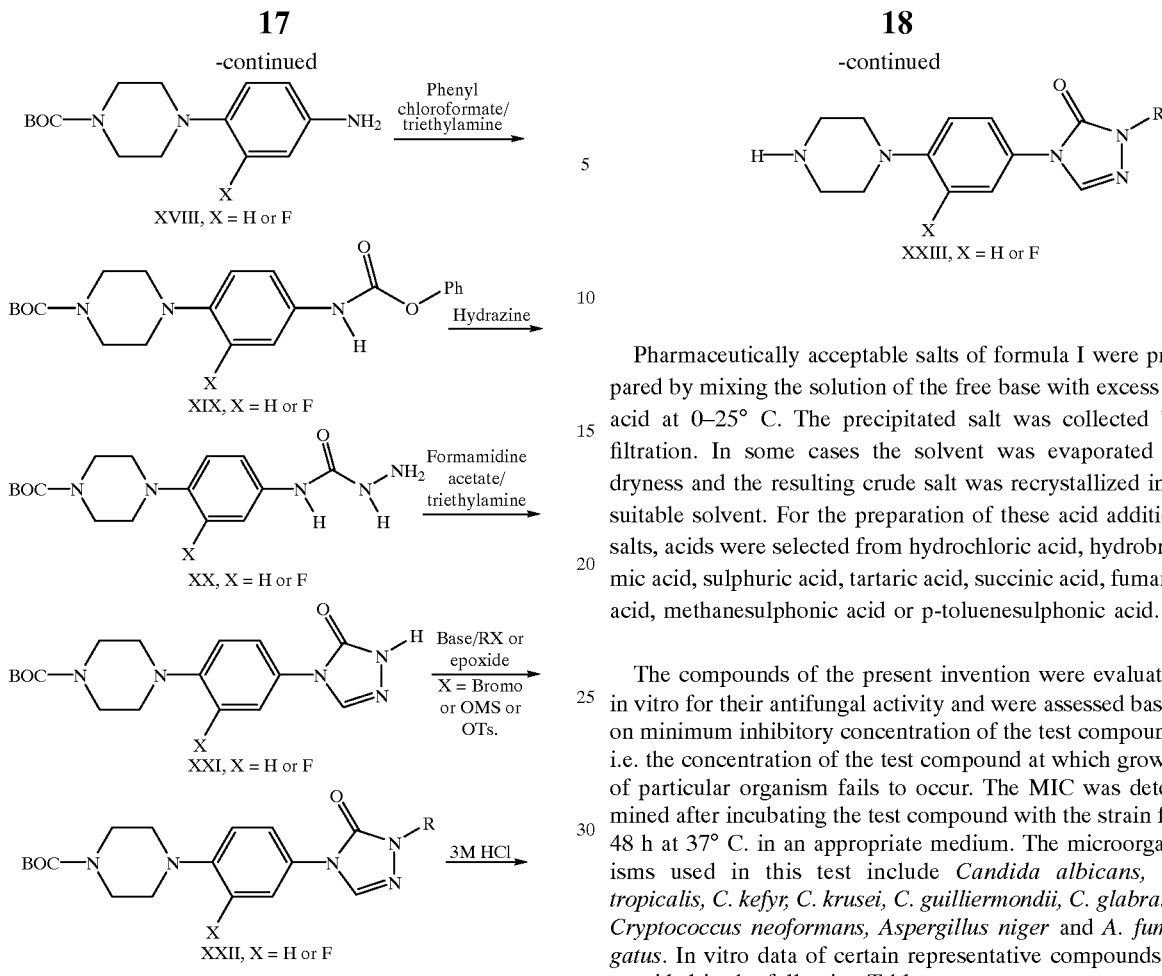

Pharmaceutically acceptable salts of formula I were prepared by mixing the solution of the free base with excess of acid at 0–25° C. The precipitated salt was collected by filtration. In some cases the solvent was evaporated to dryness and the resulting crude salt was recrystallized in a suitable solvent. For the preparation of these acid addition salts, acids were selected from hydrochloric acid, hydrobromic acid, sulphuric acid, tartaric acid, succinic acid, fumaric acid, methanesulphonic acid or p-toluenesulphonic acid.

The compounds of the present invention were evaluated in vitro for their antifungal activity and were assessed based on minimum inhibitory concentration of the test compound, i.e. the concentration of the test compound at which growth of particular organism fails to occur. The MIC was determined after incubating the test compound with the strain for 48 h at 37° C. in an appropriate medium. The microorganisms used in this test include *Candida albicans, C. tropicalis, C. kefyr, C. krusei, C. guilliermondii, C. glabrata, Cryptococcus neoformans, Aspergillus niger* and *A. fumigatus*. In vitro data of certain representative compounds is provided in the following Table.

TABLE 1

In vitro activity of compounds of formula I

| Fungal strains | MIC of compounds of formula I, µg/ml | | | | | | | Fluco-nazole | Itraco-nazole |
|---|---|---|---|---|---|---|---|---|---|
| | #36 | #40 | #41 | #42 | #43 | #44 | #46 | | |
| Candida albicans | 0.09 | 0.09 | 0.09 | 0.09 | 0.048 | 0.048 | 0.048 | 0.78 | 0.09 |
| C. tropicalis | 0.09 | 0.048 | 0.09 | 0.09 | 0.048 | 0.048 | 0.048 | 0.39 | 0.09 |
| C. kefyr | 0.048 | 0.048 | 0.48 | 0.048 | 0.048 | 0.048 | 0.048 | 0.39 | 0.09 |
| C. krusei | 0.09 | 0.19 | 1.56 | 1.56 | 0.09 | 0.09 | 0.19 | 50 | 0.39 |
| C. guilliermondii | 0.048 | 0.048 | 0.048 | 0.09 | 0.09 | 0.048 | 0.048 | 1.56 | 0.19 |
| C. glabrata | 0.09 | 0.39 | 0.78 | 12.5 | 0.78 | 1.56 | 0.39 | 12.5 | 0.19 |
| Cryptococcus neoformans | 0.048 | 0.48 | 0.48 | 0.19 | 0.048 | 0.048 | 0.048 | 1.56 | 0.39 |
| Saccheromyces cerevisiae | 0.19 | 0.09 | 0.19 | 0.39 | 0.09 | 0.048 | 0.09 | 6.25 | 0.39 |
| A. niger | 0.78 | 0.78 | 3.12 | 3.12 | 0.19 | 0.19 | 0.09 | >100 | 0.39 |
| Aspergillus fumigatus | 0.39 | 0.39 | 0.78 | 0.39 | 0.19 | 0.048 | 0.048 | >100 | 0.19 |

Certain selected compounds were evaluated in-vivo for their antifungal efficacy. Series of doses of test compounds were administered by oral, i.v and s.c. routes to infected mice, i.e mice that are inoculated with a strain of *Candida albicans* or *Aspergillus fumigatus*. Efficacy of test compound was determined based on survival of treated mice compared to control. The in vivo efficacy was assessed based on $ED_{50}$ of the test compound. The following table provides $ED_{50}$ of certain compounds for systemic infections of *C. albicans* and *A. fumigatus* in mice models.

TABLE 2

In-vivo activity of compounds of formula I

| Example # | Therapeutic efficacy ($ED_{50}$ mg/kg) in mice systemic infectinons | |
|---|---|---|
| | C. albicans | A. fumigatus |
| 36 | 8.01 | >45 |
| 40 | 4.68 | 67.05 |
| 41 | 8.01 | 89.28 |
| 42 | >90 | 71.14 |
| 43 | 1.57 | 42.3 |
| 46 | 56.02 | >45 |

The compounds of formula I and their salts are antifungal agents, useful to treat or prevent topical, lung invasive, as well as systemic fungal infections in mammals including humans. For example they are useful in treating topical infections in man caused by species of Candida, Trichophyton, Microsporum, mucosal infections caused by species of Candida, and systemic infections caused by species of Candida, Aspergillus, Cryptococcus, Pneumocystis, Histoplasma or Blastomyces. The above compounds have shown impressive in vivo efficacy against mice systemic candidiosis, systemic aspergillosis and lung invasive aspergillosis.

When the compounds of the present invention or their pharmaceutically acceptable salts are used for treatment or prophylaxis of fungal infections in mammals including humans, they can be administered alone, but generally it is more preferred to administer the compounds in a pharmaceutical formulation. This formulation varies with intended route of administration. For example the compounds can be administered orally in the form of tablets, coated tablets, capsules, suspensions, solutions and the like. These oral preparations which contain the present compounds are prepared with excipients, binders, coloring agents, flavors, etc. which can be formulated in a manner known in the art.

The present compounds can be injected parenterally, for example intravenously, intramuscularly or subcutaneously. These injections are sterile aqueous solutions which contain the antifungal agent with other substances, such as salts, glucose or an isotonic agent, and can be formulated in a conventional manner.

The amount of the present compounds incorporated into the pharmaceutical composition varies depending on the physical and chemical properties of the drug, dosage and route of administration. Preferably the oral formulations are prepared with 1 to 25% (w/w) antifungal agent and the injection formulation is prepared with 0.1 to 5% (w/w) of antifungal agent.

Alternatively, the antifungal agents also can be administered in the form of a suppository or pessary, or they may be applied topically in the form of lotion, solution, ointment, cream or dusting powder. Suppositories and ointments which contain 1–10% of active ingredient with a base, stabilizer or surfactant can be prepared in a conventional manner.

The dosage of the compound of formula I or its pharmaceutically acceptable salt can be suitably determined depending on the indivdual cases, taking symptoms, age, sex, disease status, patient condition, route of administration and the like into consideration. Usually the dosage can be 0.01–20 mg /kg in single or divided daily doses.

TABLE 3

| Example # | $R_3$ | $R_5$ | X—$R_7$ | Configuration at $C_2$ and $C_3$ |
|---|---|---|---|---|
| 1 | H | H | —COOEt | R, R |
| 2 | H | H | —H | R, R |
| 3 | H | H | —CN | R, R |
| 4 | H | H | —CHO | R, R |
| 5 | —$CH_3$ | —$CH_3$ | —H | R, R |
| 6 | —$CH_3$ | —$CH_3$ | —COOEt | R, R |
| 7 | H | H | (tert-butyl ester group) | R, R |

TABLE 3-continued

[Structure: 1-(1,2,4-triazol-1-yl)-2-(2,4-difluorophenyl)-2-hydroxy-3-methyl-3-[4-(X-R7)piperazin-1-yl]butane, with C2 and C3 labeled]

| Example # | X—R7 | Configuration at $C_2$ and $C_3$ |
|---|---|---|
| 8 | C(O)NH-phenyl | R, R |
| 9 | C(O)NH-CH₂CH₃ | R, R |
| 10 | C(O)NH-phenyl | R, R |
| 11 | C(O)NH-CH₂CH₃ | R, R |
| 12 | C(O)-(2,4-difluorophenyl) | R, R |
| 13 | C(O)-(4-CF₃-phenyl) | R, R |
| 14 | C(O)-(4-NO₂-phenyl) | R, R |
| 15 | C(O)-(4-NH₂-phenyl) | R, R |

TABLE 3-continued
| | | Configuration |
|---|---|---|
| 16 | 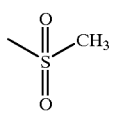 | R, R |
| 17 | 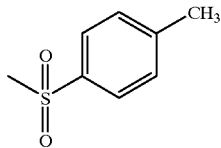 | R, R |
| 18 | 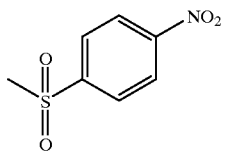 | R, R |
| 19 | 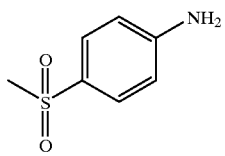 | R, R |
| 20 | 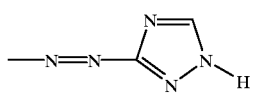 | R, R |
| 21 | 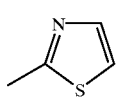 | R, R |
| 22 | 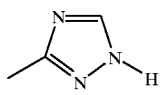 | R, R |
| 23 | 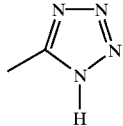 | R, R |
| Example # | X = bond; $R_7$ | Configuration at $C_2$ and $C_3$ |
|---|---|---|
| 24 | 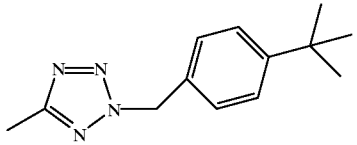 | R, R |
| 25 | 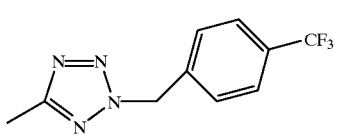 | R, R |

TABLE 3-continued
| | | |
|---|---|---|
| 26 | 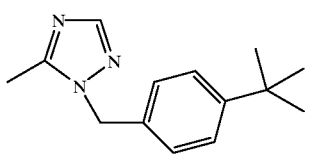 | R, R |
| 27 | 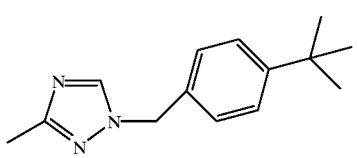 | R, R |
| 28 | 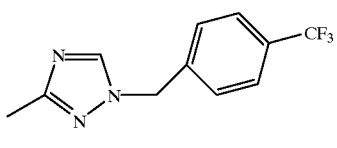 | R, R |
| 29 | 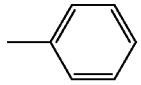 | R, R |
| 30 | 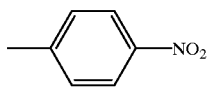 | R, R |
| 31 | 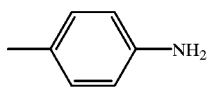 | R, R |
| 32 | 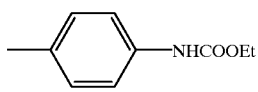 | R, R |
| 33 | 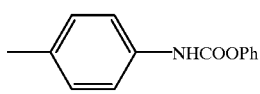 | R, R |
| 34 | 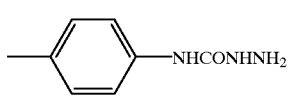 | R, R |
| 35 | 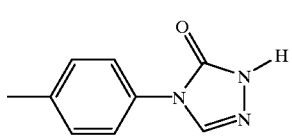 | R, R |
| 36 | 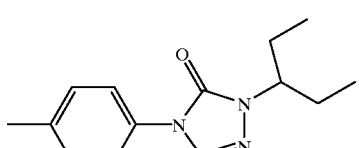 | R, R |

TABLE 3-continued
| | | |
|---|---|---|
| 37 | 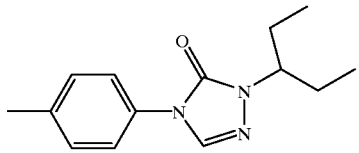 | S, R |
| 38 | 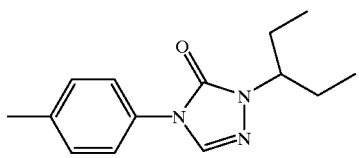 | S, S |
| 39 | 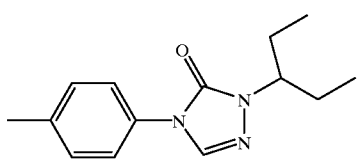 | R, S |
| 40 | 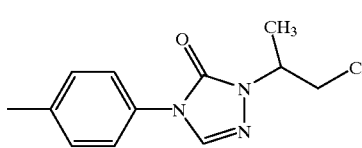 | R, R |
| 41 | 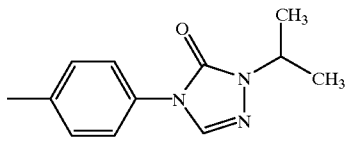 | R, R |
| 42 | 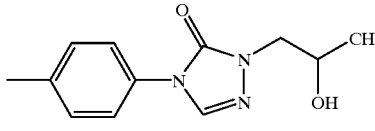 | R, R |
| 43 | 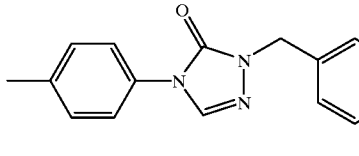 | R, R |
| 44 | 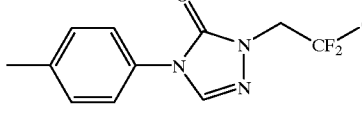 | R, R |
| 45 | 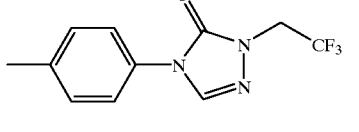 | R, R |
| 46 | 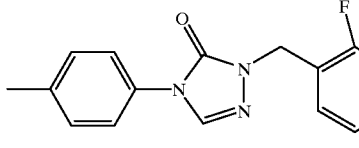 | R, R |

TABLE 3-continued

| # | Structure | Config |
|---|---|---|
| 47 | (tolyl)-triazolone-CH2-(4-OCF3-phenyl) | R, R |
| 48 | (tolyl)-triazolone-CH2-(4-OCH3-phenyl) | R, R |
| 49 | (tolyl)-triazolone-CH2-(2,4-bis-CF3-phenyl) | R, R |
| 50 | (tolyl)-triazolone-CH2-(4-OCH2CF2CF2H-phenyl) | R, R |
| 51 | (3-F-4-methylphenyl)-triazolone-CH2-(4-CF3-phenyl) | R, R |

EXAMPLES

Example 1

(2R,3R)-2-(2,4-Difluorophenyl)-3-(4-ethoxycarbonylpiperazin-1-yl)-1-(1H-1,2,4-triazol-1-yl)butan-2-ol:

A mixture of (2R,3S)-2-(2,4-difluorophenyl)-3-methyl-2-(1H-1,2,4-triazol-1-yl)methyloxirane IV (1.0 g, 4.0 mmol), ethyl piperazine-1-carboxylate (1.2 ml, 8 mmol) and potassium carbonate in DMF (5 ml) was heated at 120° C. for 18 h. After cooling the reaction mixture was poured onto crushed ice and extracted with ethyl acetate (3×30 ml). The combined extract was washed with water, brine, dried (MgSO$_4$) and concentrated and the resulting product was purified on a column of silica gel (hexane/EtOAc, 1:1) to give the title compound as off-white solid (400 mg, 24%). m.p.: 182–183° C.

$^1$H NMR (CDCl$_3$) δ: 0.90 (d, 3H, CH$_3$), 1.26 (t, 3H, CH$_3$), 2.31–2.49 (m, 2H, CH$_2$), 2.78–3.07 (m, 3H, CH$_2$ and CH), 3.40–3.59 (m, 4H, 2XCH$_2$), 4.15 (q, 2H, OCH$_2$), 4.9 (AB q, 2H, CH$_2$), 5.05 (s, 1H, OH), 6.66–6.84 (m, 2H, Ar—H), 7.36–7.51 (m, 1H, Ar—H), 7.78 (s, 1H, Het-H), 7.92 (s, 1H, Het-H).

FAB-MS: 410.2 (MH$^+$), calcd. C$_{19}$H$_{25}$F$_2$N$_5$O$_3$ 409.44.

Example 2

(2R,3R)-2-(2,4-Difluorophenyl)-3-(piperazin-1-yl)-1-(1H-1,2,4-triazole-1-yl)butan-2-ol:

A mixture of (2R,3S)-2-(2,4-difluorophenyl)-3-methyl-2-(1H-1,2,4-triazol-1-yl)methyloxirane (1.0 g, 4.0 mmol), piperazine (860 mg, 10 mmol) and lithium perchlorate (625 mg, 6 mmol) in acetonitrile (15 ml) was heated under reflux for 48 h. The solvent was removed under reduced pressure, the residue was treated with crushed ice and extracted with ethylacetate (3×30 ml). The combined organic extract was washed with water, brine, dried (Na$_2$SO$_4$) and concentrated to give the title compound as thick viscous gum (1.5 g, 78%). The title compound was also prepared by hydrolysis of 2R,3R-2-(2,4-difluorophenyl)-3-(4-ethoxycarbonylpiperazin-1-yl)-1-(1H-1,2,4-triazol-1-yl)butan-2-ol 1 with 2M sodium hydroxide solution.

$^1$H NMR (CDCl$_3$) δ: 0.97 (d, 3H, CH$_3$), 2.32–2.42 (m, 2H, CH$_2$), 2.66–2.90 (complex, 8H, 3XCH$_2$, CH and NH), 4.85 (AB q, 2H, CH$_2$), 6.68–6.83 (m, 2H, Ar—H), 7.42–7.55 (m, 1H, Ar—H), 7.78 (s, 1H, Het-H), 8.0 (s, 1H, Het-H).

FAB-MS: 338.1 (MH$^+$), calcd. C$_{16}$H$_{21}$F$_2$N$_5$O 337.38.

Example 3

(2R,3R)-3-(4-Cyanopiperazin-1-yl)-2-(2,4-diflurophenyl)-1-(1H-1,2,4-triazol-1-yl)butan-2-ol:

To a cooled (0° C.) mixture of (2R,3R)-2-(2,4-difluorophenyl)-3-(piperazin-1-yl)-1-(1H-1,2,4-triazol-1-yl)butan-2-ol 2 (250 mg, 0.74 mmol) and triethylamine (0.42 ml, 3 mmol) in acetonitrile (15 ml) was added cyanogen bromide (160 mg, 1.5 mmol) in acetonitrile (0.5 ml). The reaction mixture was stirred at room temperature for 18 h. The solvent was removed under reduced pressure. To the resulting residue water was added and extracted with ethyl acetate (3×20 ml). The combined organic extract was washed with water, brine and dried over magnesium sulphate. The solvent was removed and the product was purified on a column of silica gel (hexane/EtOAc, 1:1) to give the title compound as a colorless solid (150 mg, 56%).
m.p: 220° C. (decomp).
IR (Nujol) Vmax: 2210 cm$^{-1}$.
$^1$H NMR (CDCl$_3$) δ: 0.89 (d, 3H, CH$_3$), 2.52–2.61 (m, 2H, CH$_2$), 3.0–3.31 (m, 7H, 3XCH$_2$ and CH), 4.88–4.91 (m, 3H, CH$_2$ and OH), 6.66–6.78 (m, 2H, Ar—H), 7.3–7.5 (m, 1H, Ar—H), 7.78 (s, 1H, Het-H), 7.87 (s, 1H, Het-H).
FAB-MS: 363.0 (MH$^+$), calcd. C$_{17}$H$_{20}$F$_2$N$_6$O 362.39.

Example 4

(2R,3R)-2-(2,4-Difluorophenyl)-3-(4-formylpiperazin-1-yl)-1-(1H-1,2,4-triazol-1-yl)butan-2-ol:

A mixture of compound 2 (200 mg, 0.6 mmol) and potassium carbonate (248 mg, 1.8 mmol) in DMF (5 ml) was heated at 120° C. for 24 h. The contents were poured into cold water and extracted with ethyl acetate (3×20 ml). The combined organic extract was washed with water, brine and dried over sodium suphate. The solvent was removed under reduced pressure and the resulting product was purified on a column of silica gel (EtOAc/MeOH; 98:2) to give the title compound as colorless solid (80 mg, 36%).
m.p: 118–120° C.
$^1$H NMR (CDCl$_3$) δ: 0.90 (d, 3H, CH$_3$), 2.44–2.52 (m, 2H, CH$_2$), 2.93–3.11 (m, 3H, CH$_2$ and CH), 3.39–3.59 (m, 4H, 2XCH$_2$), 4.93–4.97 (m, 3H, CH$_2$ and OH), 6.66–6.81 (m, 2H, Ar—H), 7.36–7.48 (m, 1H, Ar—H), 7.79 (s, 1H, Het-H), 7.91 (s, 1H, Het-H), 8.02 (s, 1H, CHO).
FAB-MS: 366.1 (MH$^+$), calcd. C$_{17}$H$_{21}$F$_2$N$_5$O$_2$ 365.39.

Example 5

(2R,3R)-2-(2,4-Difluorophenyl)-3-(2,5-dimethylpiperazin-1-yl)-1-(1H-1,2,4-triazol-1-yl)butan-2-ol:

The title compound 5 was obtained as a thick viscous oil in 58% yield from the reacton of (2R,3S)-2-(2,4-difluorophenyl)-3-methyl-2-(1H-1,2,4-triazol-1-yl) methyloxirane IV and 2,5-dimethylpiperazine, by a similar method described in example 2.
$^1$H NMR (CDCl$_3$) δ: 0.85–0.96 (3 d merged, 9H, 3XCH$_3$), 1.85–1.96 (m, 2H), 2.4–2.59 (m, 2H), 2.64–2.96 (m, 3H), 3.27–3.38 (m, 1H), 4.81 (AB q, 2H, CH$_2$), 5.50 (brs, 1H, OH), 6.69–6.84 (m, 2H, Ar—H), 7.45–7.58 (m, 1H, Ar—H), 7.81 (s, 1H, Het-H), 8.02 (s, 1H, Het-H).
FAB-MS: 366.1 (MH$^+$), calcd. C$_{18}$H$_2$, F$_2$N, O 365.43.

Example 6

(2R,3R)-2-(2,4-Difluorophenyl)-3-(2,5-dimethyl-4-ethoxycarbonylpiperazin-1-yl)-1-(1H-1,2,4-triazol-1-yl) butan-2-ol:

To a mixture of compound 5 (228 mg, 0.62 mmol) and triethylamine (0.18 ml, 1.24 mmol) in dichloromethane (10 ml) at 0° C. was added dropwise ethyl chloroformate (135 mg, 1.24 mmol) in dichloromethane (3 ml). The reaction mixture was stirred at 0° C. for 30 minutes and 1 h at room temperature. The contents were diluted with 30 ml of dichloromethane, washed with water, brine and dried over magnesium sulphate. The solvent was removed under reduced pressure and the resulting oil was chromatographed on a column of silica gel. Elution with hexane/EtOAc (1:1) gave the title compound as an off-white solid (210 mg, 80%).
m.p: 57–59° C.
$^1$H NMR (CDCl$_3$) δ: 0.94 (d, 3H, CH$_3$), 1.07–1.10 (m, 6H, 2XCH$_3$), 1.28 (t, 3H, CH$_3$), 2.34–2.46 (m, 1H), 2.76–2.82 (m, 1H), 2.96–3.09 (m, 2H), 3.21–3.31 (m, 1H), 3.67 (m, 1H), 3.98–4.27 (m, 3H), 4.80 (AB q, 2H), 5.13 (s, 1H, OH), 6.67–6.82 (m, 2H, Ar—H), 7.39–7.52 (m, 1H, Ar—H), 7.78 (s, 1H, Het-H), 7.94 (s, 1H, Het-H).
FAB-MS: 438.3 (MH$^+$), calcd. C$_{21}$H$_{29}$F$_2$N$_5$O$_3$ 437.49.

Example 7

(2R,3R)-3-(4-tert-BOC-Piperazin-1-yl)-2-(2,4-difluorophenyl)-1-(1H-1,2,4-triazol-1-yl)butan-2-ol:

To a mixture of compound 2 (150 mg, 0.44 mmol) and triethylamine (1.0 ml, 0.72 mmol) in dichloromehane (15 ml) was added di-tert-butyldicarbonate (110 mg, 0.48 mmol) at ° C. The reaction mixture was stirred for 1 h at 0° C. and 3 h at room temperature. Then diluted with chloroform (20 ml), washed with water, brine and dried over sodium sulphate. The solvent was removed under reduced pressure and the resulting product was purified on a column of silica gel (EtOAc/hexane) to give the title compound as a colorless solid (160 mg, 82%).
m.p.: 138–139° C.
$^1$H NMR (CDCl$_3$) δ: 0.92 (d, 3H, CH$_3$), 1.46 (s, 9H, 3XCH$_3$), 2.34–2.40 (m, 2H, CH$_2$), 2.79–2.92 (m, 2H, CH$_2$), 2.97 (m, 1H, CH), 3.43 (m, 4H, 2XCH$_2$), 4.88 (AB q, 2H, CH$_2$), 5.11 (s, 1H, OH), 6.66–6.80 (m, 2H, Ar—H), 7.38–7.51 (m, 1H, Ar—H), 7.78 (s, 1H, Het-H), 7.94 (s, 1H, Het-H).
FAB-MS 438.2 (MH$^+$); calcd. C$_{21}$H$_{29}$F$_2$N$_5$O$_3$ 437.49.

Example 8

(2R,3R)-3-(4-Anilinocarbonylpiperazin-1-yl)-2-(2,4-difluorophenyl)-1-(1H-1,2,4-triazol-1-yl)butan-2-ol:

To a ice cooled solution of (2R,3R)-2-(2,4-difluorophenyl)-3-(piperazin-1-yl)-1-(1H-1,2,4-triazole-1-yl) butan-2-ol 2 (150 mg, 0.44 mmol) in acetonitrile (10 ml) was added phenylisocyanate (60 mg, 0.5 mmol) in acetonitrile (4 ml). The reaction mixture was stirred at 0° C. for 2 h, diluted with 20 ml of ethyl acetate and successively washed with water, brine and dried over sodium sulphate. This organic extract was concentrated and the residue was purified by passing through a column of silica gel (hexane/EtOAc) to give the title compound as a colorless solid (170 mg, 84%).
m.p.: 98–100° C. (decomp).
$^1$H NMR (CDCl$_3$) δ: 0.92 (d, 3H, CH$_3$), 2.5 (m, 2H, CH$_2$), 3.02 (m, 3H, CH$_2$ and CH), 3.52 (m, 4H, 2XCH$_2$), 4.8–5.1 (AB q and S merged, 3H, CH$_2$ and OH), 6.31 (brs, 1H, NH), 6.65–6.85 (m, 2H, Ar—H), 7.0–7.1 (m, 1H, Ar—H), 7.25–7.5 (m, 5H, Ar—H), 7.78 (s, 1H, Het-H), 7.92 (s, 1H, Het-H).
MS (FAB): 457.0 (MH$^+$), calcd. C$_{23}$H$_{26}$F$_2$N$_6$O$_2$ 456.49.

Example 9

(2R,3R)-2-(2,4-Difluorophenyl)-3-(4-ethylaminocarbonylpiperazin-1-yl)-1-(1H-1,2,4-triazol-1-yl)butan-2-ol:

The tiltle compound was prepared similarly to example 8 starting from same piperazine derivative and ethylisocyanate. The product was obtained as a colorless solid in 75% yield.
m.p.: 103–105° C.
$^1$H NMR (CDCl$_3$) δ: 0.9 (d, 3H, CH$_3$), 1.14 (t, 3H, CH$_3$), 2.42 (m, 2H, CH$_2$), 2.8–3.1 (m and q merged, 3H, CH$_2$ and CH), 3.2–3.5 (m, 6H, 3XCH$_2$), (4.4 brs, 1H, NH), 4.88 (AB q, 2H, CH$_2$), 5.06 (s, 1H, OH), 6.7–6.9 (m, 2H, Ar—H), 7.45 (m, 1H, Ar—H), 7.78 (s, 1H, Het-H), 7.93 (s, 1H, Het-H).
FAB-MS: 409.1 (MH$^+$), calcd. C$_{19}$H$_{26}$F$_2$N$_6$O$_2$ 408.45.

Example 10
(2R,3R)-3-(4-Anilinothiocarbonylpiperazin-1-yl)-2-(2,4-difluorophenyl)-1-(1H-1,2,4-triazol-1-yl)butan-2-ol:

The title compound was prepared similarly to example 8 starting from same piperazine derivative 2 and phenylisothiocyanate. The product was obtained as a colorless solid in 80% yield.

m.p.: 106–108° C.

$^1$H NMR (CDCl$_3$) δ: 0.88 (d, 3H, CH$_3$), 2.5 (m, 2H, CH$_2$), 2.9–3.1 (m, 3H, CH$_2$ and H), 3.84 (m, 4H, 2XCH$_2$), 4.8–5.1 (AB q and s merged, CH$_2$ and OH), 6.7–6.85 (m, 2H, Ar—H), 7.1–7.5 (m, 7H, 6 Ar—H and 1 NH), 7.77 (s, 1H, Het-H), 7.88 (s, 1H, Het-H).

FAB-MS: 473.3 (MH$^+$), calcd. C$_{23}$H$_{26}$F$_2$N$_6$OS 472.56.

Example 11
(2R,3R)-2-(2,4-Difluorophenyl)-3-(4-ethylaminothiocarbonylpiperazin-1-yl)-1-(1H-1,2,4-triazol-1-yl)butan-2-ol:

The title compound was prepared similarly to example 8 starting from same piperazine derivative 2 and ethylthioisocyanate. The product was obtained as a colorless solid in 85% yield.

m.p.: 96–98° C.

$^1$H NMR (CDCl$_3$) δ: 0.88 (d, 3H, CH$_3$), 1.25 (t, 3H, CH$_3$), 2.5 (m, 2H, CH$_2$), 3.06 (m, 3H, CH$_2$ and CH), 3.6–4.0 (q and m merged, 6H, 3XCH$_2$), 4.8–5.0 (AB q and s merged, 3H, CH$_2$ and OH), 5.39 (s, 1H, NH), 6.7–6.9 (m, 2H, Ar—H), 7.4–7.5 (m, 1H, Ar—H), 7.78 (s, 1H, Het-H), 7.89 (s, 1H, Het-H).

FAB-MS: 425.1 (MH$^+$), calcd. C$_{19}$H$_{26}$F$_2$N$_6$OS 424.51.

Example 12
(2R,3R)-3-[4-(2,4-Difluorobenzoyl)piperazin-1-yl]2-(2,4-difluorophenyl)-1-(1H-1,2,4-triazol-1-yl)butan-2-ol.

To a mixture of compound 2 (674 mg, 2 mmol) and triethylamine (0.55 ml, 4 mmol) in tetrahydrofuran (10 ml) was added dropwise 2,4-difluorobezoyl chloride (440 mg, 2.5 mmol) in 5 ml tetrahydrofuran at 0° C. The reaction mixture was stirred at 0° C. for 30 minutes and at room temperature for 18 h. The solvent was removed under reduced pressure, the residue was dissolved in dichloromethane (50 ml). The organic phase was washed with brine, dried over sodium sulphate. The solvent was removed under reduced pressure and the resulting product was purified on a column of silica gel (EtOAc/hexane, 9:1) to give the title compound as colorless prisms (448 mg, 47%).

m.p.=63–65° C.

$^1$H NMR (CDCl$_3$) δ: 0.88 (d, J=6.1 Hz, 3H), 2.04–2.59 (m, 2H); 2.99–3.09 (m, 4H); 3.35 (s, 2H); 3.72–4.10 (m, 1H) 4.91 (s, 2H); 5.01 (s, 1H); 6.65–7.00 (m, 5H); 7.34–7.48 (m, 1H); 7.77 (s, 1H); 7.9 (s, 1H).

FAB-MS: 478.3 (MH$^+$), calcd. C$_{23}$H$_{23}$F$_4$N$_5$O$_2$ 477.46.

Example 13
(2R,3R)-2-(2,4-Difluorophenyl)-1 (1H-1,2,4-triazol-1-yl)-3-[4-(4-trifluoromethylbenzoyl)piperazin-1-yl]butan-2-ol.

The example 13 was prepared form the reaction of piperazino derivative 2 and 4-(trifluoromethyl)benzoyl chloride by following the similar procedure described for the example 12.

Colorless prisms, m.p.: 88–90° C., Yield 87%.

$^1$H NMR (CDCl$_3$) δ: 0.88 (d, J=6.5 Hz, 3H); 2.39–2.59 (m, 2H) 3.00–3.10 (m, 4H); 3.41–3.73 (m, 4H); 4.83 (AB q, 2H) 6.65–6.79 (m, 2H); 7.35–7.47 (m, 1H); 7.49 (d, J=8.0 Hz, 2H) 7.66 (d, J=8.0 Hz, 2H); 7.78 (s, 1H), 7.91 (s, 1H).

FAB-MS: 510.1 (MH$^+$), Calcd. C$_{24}$H$_{24}$F$_5$N$_5$O$_2$ 509.48.

Example 14
(2R,3R)-2-(2,4-Difluorophenyl)-3-[4-(4-nitrobenzoyl)piperazin-1-yl]1-(1H-1,2,4-triazol-1-yl)butan-2-ol The example 14 was prepared form the reaction of piperazino derivative 2 and 4-nitrobenzoyl chloride by following the similar procedure described for the example 12. After column purification the product was obtained as brown prisms in 92% yield.

m.p. 90–92° C.

$^1$H NMR (CDCl$_3$) δ: 0.88 (d, J=6.5 Hz, 3H), 2.42–2.61 (m, 2H) 3.05–3.08 (m, 4H); 3.39–3.73 (m, 3H); 4.92 (s, 3H) 6.66–6.78 (m, 2H); 7.34–7.47 (m, 1H); 7.55 (d, J=8.6 Hz, 2H) 7.77 (s, 1H); 7.88 (s, 1H); 8.26 (d, J=8.6 Hz, 2H).

FAB-MS: 487.0 (MH$^+$), C$_{23}$H$_{24}$F$_2$N$_6$O$_4$ 486.42.

Example 15
(2R,3R)-3-[4-(4-Aminobenzoyl)piperazin-1-yl]2-(2,4-difluorophenyl)-1-(1H-1,2,4-triazol-1-yl)butan-2-ol A solution of nitrocompound 14 (487 mg, 1.0 mmol) in ethyl acetate (95 ml) was hydrogenated over 10% Pd—C (50 mg) at 45 psi pressure and room temperature for 6 h. The catalyst was removed by filtration and the filtrate was concentrated to give the amino compound 15 as a colorless solid (330 mg, 72%).

m.p.: 100–102° C.

$^1$H NMR (CDCl$_3$) δ: 0.89 (d, J=5.8 Hz, 3H); 2.42–2.47 (m, 2H) 2.88–3.06 (m, 3H); 3.63 (br, 4H); 3.09 (br, 2H) 4.82 (t, J=16.3 Hz, 2H); 5.02 (br, 1H); 6.61 (d, J=8.5 Hz, 2H) 6.73–6.79 (m, 2H); 7.22 (d, J=8.5 Hz, 2H); 7.30–7.48 (m, 1H) 7.77 (s, 1H); 7.92 (s, 1H).

FAB-MS: 457.1 (MH$^+$), calcd. C$_{23}$H$_{26}$F$_2$N$_6$O$_2$ 456.46.

Example 16
(2R,3R)-2-(2,4-Difluorophenyl)-3-[4-(p-toluenesulphonyl)piperazin-1-yl]-1-(1H-1,2,4-triazol-1-yl)butan-2-ol:

To a mixture of piperazinyl compound 2 (146 mg, 0.43 mmol) and triethylamine in dichloromethane (5 ml) was added p-toluenesulphonyl chloride (51 mg, 0.45 mmol) in dichloromethane (1 ml) at 0° C. The reaction mixture was stirred at 0° C. for 15 minutes and 2 h at room temperature. Then the reaction mixture was diluted with chloroform (15 ml), washed with water, brine and dried over sodium sulphate. The solvent was removed under reduced pressure and the resulting product was purified on a column of silica gel (CHCl$_3$/MeOH; 98:2 ) to give the title compound as a colorless solid (75 mg, 16%).

m.p.: 81–83° C.

$^1$H NMR (CDCl$_3$) δ: 0.88 (d, J=6.9 Hz, 3H), 2.44 (s, 3H), 2.48–2.57 (m, 2H), 2.92–3.08 (m, 7H), 4.74 (s, 2H), 4.83 (s, 1H), 6.64–6.76 (m, 2H), 7.29–7.36 (m, 3H), 7.63 (s, 1H), 7.68 (s, 1H), 7.74 (s, 1H), 7.80 (s, 1H).

FAB-MS: 491.9 (MH$^+$), calcd. C$_{23}$H$_{27}$F$_2$N$_5$O$_3$S 491.55.

Example 17
(2R,3R)-2-(2,4-Difluorophenyl)-3-[4-(methanesulphonyl)piperazin-1-yl]-1-(1H-1,2,4-triazol-1-yl)butan-2-ol:

The epoxide IV (300 mg, 1.19 mmol) and LiClO$_4$ (235 mg, 1.43 mmol) were dissolved in 12 mL dry acetonitrile and 1-methanesulfonylpiperazine (190 mg, 1.79 mmol) was added. The mixture was heated to reflux for 4 days, cooled and the solvent evaporated. The residue was dissolved in dichloromethane and then washed with water and brine. The solution was dried over Na$_2$SO$_4$ and the solvent evaporated. The crude reaction products were eluted through a silica gel column using 3% MeOH/97% EtOAc as eluent to give the title compound (180 mg, 36%) as a colorless solid.

m.p.: 83–85° C.

$^1$H NMR (CDCl$_3$) δ: 0.91 (d, J=6.4 Hz, 3H), 2.56–2.61 (m, 2H), 2.80 (s, 3H), 3.02–3.18 (m, 3H), 3.22–3.30 (m, 4H), 4.89 (s, 2H), 4.93 (s, 1H), 6.66–6.79 (m, 2H), 7.35–7.48 (m, 1H), 7.79 (s, 1H), 7.88 (s, 1H).
FAB-MS: 415.9 (MH$^+$), C$_{17}$H$_{23}$F$_2$N$_5$O$_3$S 415.45

Example 18
(2R,3R)-2-(2,4-Difluorophenyl)-3-[4-(4-nitrophenylsulphonyl)piperazin-1-yl]-1-(1H-1,2,4-triazol-1-yl)butan-2-ol.:

The title compound was prepared from piperazinyl compound 2 and p-nitrobenzenesulphonyl chloride by following the similar procedure described for example 12. The product was obtained as tan needles in 38% yield after purification on a column of silica gel (CHCl$_3$/MeOH; 96:4) followed by recrystalization in ether.
m.p.: 160–162° C.
$^1$H NMR (CDCl$_3$) δ: 0.87 (d, J=6.7 Hz, 3H), 2.51–2.66 (m, 2H), 2.96–3.20 (m, 7H), 4.74 (s, 2H), 4.81 (s, 1H), 6.62–6.76 (m, 2H), 7.29–7.41 (m, 1H), 7.72 (s, 1H), 7.77 (s, 1H), 7.94–7.98 (m, 2H), 8.39–8.43 (m, 2H).
FAB-MS: 523.2 (MH$^+$), calcd. C$_{22}$H$_{24}$F$_2$N$_6$O$_5$S 522.52.

Example 19
(2R,3R)-3-[4-(4-aminophenylsulphonyl)piperazin-1-yl]-2-(2,4-difluorophenyl)-1-(1H-1,2,4-triazol-1-yl)butan-2-ol:

A solution of nitrocompound 18 (230 mg, 0.44 mmol) in ethanol (10 ml) was hydrogenated over 10% Pd—C (25 mg) at 45 psi pressure and room temperature for 18 h. The catalyst was removed by filtration and the filtrate was concentrated and the resulting product was purified on a column of silica gel (CHCl$_3$/MeOH; 57:43) to give the amino compound 19 as a colorless solid (165 mg, 76%).
m.p.: 95–97° C.
$^1$H NMR (CDCl$_3$) δ: 0.88 (2, J=6.1 Hz, 3H), 2.48–2.58 (m, 2H), 2.96–3.09 (m, 7H), 4.14 (br, 2H), 4.75 (s, 2H), 4.86 (s, 1H), 6.63–6.77 (m, 4H), 7.31–7.43 (m, 1H), 7.52–7.57 (m, 2H), 7.74 (s, 1H), 7.83 (s, 1H).
FAB-MS: 493.5 (MH$^+$), calcd. C$_{22}$H$_{26}$F$_2$N$_6$O$_3$S 492.54.

Example 20
(2R,3R)-2-(2,4-Difluorophenyl)-3-[4-(3-azo-1H-1,2,4-triazolyl)piperazin-1-yl]1-(1H-1,2,4-triazol-1-yl)butan-2-ol:

To a cooled solution of 3-amino-1H-1,2,4-triazole (378 mg, 4.5 mmol) in concentrated hydrochloric acid (1 ml) was added sodium nitrite (310 mg, 4.5 mmol) in portions. The resulting diazonium salt was transferred to a flask containing compound 2 (1 g, 3.0 mmol) in 20 ml of 3:1 mixture of 10% sodium hydroxide solution and tetrahydrofuran. The resulting reaction mixture was stirred at room temperature for 2 h and extracted with chloroform (3×25 ml). The combined organic extract was washed with water, brine and dried over sodium sulphate. The solvent was removed under reduced pressure and the resulting product was purified on a column of silica gel to give the title compound as thick viscous gum (100 mg, 8%).
$^1$H NMR (CDCl$_3$) δ: 0.92 (d, 3H, CH$_3$), 2.65 (m, 2H, CH$_2$), 3.1–3.3 (m, 3H, CH$_2$ and CH), 4.0 (m, 4H, 2XCH$_2$), 4.95 (m, 3H, CH$_2$ and OH), 6.72–6.81 (m, 2H, Ar—H), 7.4–7.49 (m, 1H, Ar—H), 7.79 (s, 1H, Het-H), 7.91 (s, 1H, Het-H), 7.97 (s, 1H, Het-H).
FAB-MS: 433.2 (MH$^+$), calcd. C$_{18}$H$_{22}$F$_2$N$_{10}$O 432.43.

Example 21
Ethyl 4-(2-thiazolyl)piperazine-1-carboxylate:

A mixture of 2-bromothiazole (1.64 g, 10 mmol), ethyl 1-piperazinecarboxylate (1.896, 12 mmol) and sodium iodide (1.498, 10 mmol) in N,N-dimethylformamide (10 ml) was heated at 120° C. for 18 h. After cooling, the solvent was removed under reduced pressure and the residue was treated with crushed ice. The desired product was precipitated as colorless solid, was isolated by filtration (2.2 g, 91%).
$^1$H NMR (CDCl$_3$) δ: 1.28 (t, 3H, CH$_3$), 3.48 (m, 4H, 2XCH$_2$), 3.62 (m, 4H, 2XCH$_2$), 4.17 (q, 2H, OCH$_2$), 6.60 (d, 1H, Het-H, J=3.5 Hz), 7.20 (d, 1H, Het-H, J=3.5 Hz)
2-(Piperazin-1-ylthiazole:

To a methanolic solution of ethyl 4-(2-thiazolyl)piperazine-1-carboxylate (2 g, 8 mmol), 20 ml of 10% sodium hydroxide solution was added. The resulting mixture was heated under reflux for 5 h. After cooling, the reaction mixture was concentrated under reduced pressure, the residue was diluted with water and extracted with chloroform (3×30 ml). The combined extract was washed with water, brine, dried (Na$_2$SO$_4$) and concentrated to give the title compound as a thick viscous liquid (1.2 g, 86%).
$^1$H NMR (CDCl$_3$) δ: 1.68 (br s, 1H, NH), 2.98 (m, 4H, 2XCH$_2$), 3.46 (m, 2XCH$_2$), 6.56 (d, 1H, Het-H, J=3.5 Hz), 7.2 (d, 1H, Het-H, J=3.5 Hz).
(2R,3R)-2-(2,4-Difluorophenyl)-3-[4-(2-thiazolyl)piperazin-1-yl]-1-(1H-1,2,4-triazol-1-yl)butan-2-ol:

To a mixture of (2R,3S)-2-(2,4-difluorophenyl)-3-methyl-2-(1H-1,2,4-triazol-1-yl)methyloxirane IV (502 mg, 2 mmol) and lithium perchlorate (320 mg, 3 mmol) in acetonitrile (10 ml), 2-(piperazin-1-yl)thiazole (X)(507 mg, 3 mmol) was added. The resulting mixture was heated under reflux for 48 h. The reaction mixture was cooled, concentrated under reduced pressure. The residue was disolved in chloroform, washed with water, brine, dried (Na$_2$SO$_4$) and concentrated. The resulting product was purified on a column of silica gel using ethyl acetate and hexane (4:1) as eluent to give the title compound as colorless solid (650 mg, 77%).
m.p.: 180–181° C.
$^1$H NMR (CDCl$_3$) δ: 0.93 (d, 3H, CH$_3$), 2.57 (m, 2H, CH$_2$), 3.05 (m, 3H, CH$_2$ and CH) 3.51 (m, 4H, 2XCH$_2$), 4.92 (AB q, 2H, CH$_2$), 5.05 (s, 1H, OH), 6.58 (d, 1H, Het-H, J=3.5 Hz), 6.7–6.8 (m, 2H, Ar—H), 7.2 (d, 1H, Het-H, J=3.5 Hz), 7.4–7.5 (m, 1H, Ar—H), 7.78 (s, 1H, Het-H), 7.93 (s, 1-H, Het-H).
FAB-MS: 421.0 (MH$^+$), calcd. C$_{19}$H$_{22}$F$_2$N$_6$OS 420.482.

Example 22
(2R,3R)-2-(2,4-Difluorophenyl)-3-[4-(1H-1,2,4-triazol-3-yl)piperazin-1-yl]-1-(1H-1,2,4, triazol-1-yl)butan-2-ol:

The title compound was prepared in 48% yield from (2R,3S)-2-(2,4-difluorophenyl)-3-methyl-2-(1H-1,2,4-triazol-1-yl)methyloxirane and 3-(piperazin-1-yl)-1H-1,2,4-triazole (XI) in the presence of lithium perchlorate following the similar procedure described for example 21.
m.p.: 71–73° C.
$^1$H NMR (CDCl$_3$) δ: 0.91 (d, 3H, CH$_3$), 2.48–2.60 (m, 2H, CH$_2$), 2.90–3.03 (m, 3H, CH$_2$ and CH), 3.32–3.51 (m, 4H, 2XCH$_2$), 4.81–5.04 (m, 2H, CH$_2$), 5.20 (br, 2H), 6.67–6.86 (m, 2H, Ar—H), 7.35–7.58 (m, 1H, Ar—H), 7.72 (s, 1H, Het-H), 7.78 (s, 1H, Het-H), 8.01 (s, 1H, Het-H)
FAB-MS: 405.0 (MH$^+$), calcd. C$_{18}$H$_{22}$F$_2$N$_8$O 404.36.

Example 23
(2R,3R)-2-(2,4-difluorophenyl)-3-[4-(1H-5-tetrazolyl)piperazin-1-yl]-1-(1H-1,2,4, triazol-1-yl)butan-2-ol:

A mixture of compound 3 (140 mg, 0.39 mmol), sodium azide (31 mg, 0.47 mmol) and ammonium chloride (25 mg, 0.47 mmol) in DMF (5 ml) was heated at 90° C. for 48 h. Solvent was removed under reduced pressure and the residue was extracted with ethyl acetate (3×10 ml). Combined organic extract was washed with water, brine and dried over sodium sulphate. The solvent was removed under reduced pressure and the resulting product was purified on a column of silica gel to give the title compound as a off-white solid (30 mg, 19%).
m.p.: 104–105° C.
$^1$H NMR (CDCl$_3$) δ: 0.93 (d, 3H, CH$_3$), 2.63 (m, 2H, CH$_2$), 3.07 (m, 3H, CH$_2$ and CH), 3.56 (m, 4H, 2XCH$_2$), 4.93 (AB q and s merged, 3H, CH$_2$ and OH), 6.70–6.77 (m, 2H, Ar—H), 7.42–7.45 (m, 1H, Ar—H), 7.80 (s, 1H, Het-H), 7.96 (s, 1H, Het-H).
FAB-MS: 406.3 (MH$^+$), calcd. C$_{17}$H$_{21}$F$_2$N$_9$O 405.42

Example 24

(2R,3R)-2-(2,4-Difluorophenyl)-3-{4-[2-(4-tert-butylbenzyl)-2H-tetrazol-5-yl]piperazin-1-y}-1-(1H-1,2,4-triazol-1yl)butan-2-ol:

The title compound was prepared from the epoxide IV and tetrazolylpiperazine XVI (Ar=4-tetrt-butylphenyl) by following the similar procedure described for example 21.

After usual workup and column purification the title compound was obtained as a colorless solid in 36% yield.
m.p.: 99–101° C.
$^1$H NMR (CDCl$_3$) δ: 0.94 (d, 3H, CH$_3$), 1.30 (s, 9H, 3XCH$_3$), 2.47–2.59 (m, 2H, CH$_2$), 2.91–3.01 (m, 3H, CH$_2$ and CH), 3.50 (m, 4H, 2XCH$_2$), 4.88 (AB q, 2H, CH$_2$), 5.12 (br s, 1H, OH), 5.53 (s, 2H, CH$_2$), 6.67–6.81 (m, 2H, Ar—H), 7.29–7.48 (m, 5H, Ar—H), 7.79 (s, 1H, Het-H), 7.95 (s, 1H, Het-H).
FAB-MS: 552.2 (MH$^+$); calcd. C$_{28}$H$_3$ F$_2$N$_9$O 551.61.

Example 25

(2R,3R)-2-(2,4-Difluorophenyl)-1-(1H-1,2,4-triazol-1-yl)-3-{4-[2-(4-trifluoromethylbenzyl)-2H-tetrazol-5-yl]piperazin-1-yl}butan-2-ol:

The title compound was prepared from the epoxide IV and tetrazolylpiperazine XVI (Ar=4-(trifluoromethyl)phenyl) by following the similar procedure described for example 21. After usual workup and column purification the title compound was obtained as a colorless solid in 30% yield.
m.p.: 71–72° C.
$^1$H NMR (CDCl$_3$) δ: 0.93 (d, 3H, CH$_3$), 2.51–2.56 (m, 2H, CH$_2$), 2.96–3.02 (m, 3H, CH$_2$ and CH), 3.49 (m, 4H, 2XCH$_2$), 4.90 (AB q, 2H, CH$_2$), 5.07 (s, 1H, OH), 5.62 (s, 2H, CH$_2$), 6.68–6.77 (m, 2H, Ar—H), 7.43–7.65 (m, 5H, Ar—H), 7.78 (s, 1H, Het-H), 7.93 (s, 1H, Het-H).
FAB-MS: 564.1 (MH$^+$), calcd. C$_{25}$H$_{26}$F$_5$N$_9$O 563.54.

Example 26

(2R,3R)-2-(2,4-Difluorophenyl)-3-{4-[2-(4-tert-butylbenzyl)-2H-1,2,4-triazol-3-yl]piperazin-1-y}-1-(1H-1,2,4-triazol-1yl)butan-2-ol:

The title compound was prepared from the epoxide IV and triazolylpiperazine XII (Ar=4-tert-butylphenyl) by following the similar procedure described for example 21. After usual workup and column purification the title compound was obtained as a colorless solid in 45% yield.
m.p.: 73–75° C.
$^1$H NMR (CDCl$_3$) δ: 0.93 (d, 3H), 1.30 (s, 9H), 2.49–2.59 (m, 2H), 2.95–3.07 (m, 3H), 3.12–3.14 (m, 4H), 4.78–4.95 (m, 2H), 5.04 (s, 1H), 5.15 (s, 2H), 6.66–6.80 (m, 2H), 7.12 (d, 2H, J=8.3 Hz), 7.34 (d, 2H, J=8.3 Hz), 7.35–7.49 (m, 1H), 7.69 (s, 1H), 7.76 (s, 1H), 7.92 (s, 1H).
FAB-MS: 551.4 (MH$^+$), calcd. C$_{29}$H$_{36}$F$_2$N$_8$O 550.66

Example 27

(2R,3R)-2-(2,4-Difluorophenyl)-3-{4-[1-(4-tert-butylbenzyl)-1H-1,2,4-triazol-3-yl]piperazin-1-y}-1-(1H-1,2,4-triazol-1yl)butan-2-ol:

The title compound was prepared from the epoxide IV and triazolylpiperazine XIII (Ar=4-tert-butylphenyl) by follow-ing the similar procedure described for example 21. After usual workup and column purification the title compound was obtained as a colorless solid in 46% yield.
m.p.: 84–86° C.
$^1$H NMR (CDCl$_3$): δ: 0.94 (d, 3H, CH$_3$), 1.30 (s, 9H, 3XCH$_3$), 2.45–2.55 (m, 2H), 2.83–3.01 (m, 3H), 3.42–3.48 (m, 4H), 4.79–4.97 (m, 2H), 5.11 (s, 2H), 5.22 (s, 1H), 6.67–6.81 (m, 2H), 7.16 (d, 2H, J=8.2 Hz), 7.36 (d, 2H, J=8.2 Hz), 7.41–7.53 (m, 1H), 7.66 (s, 1H), 7.78 (s, 1H), 7.97 (s, 1H).
FAB-MS: 551.3 (MH$^+$), calcd. C$_{29}$H$_{36}$F$_2$N$_8$O 550.66.

Example 28

(2R,3R)-2-(2,4-Difluorophenyl) -1-(1H-1,2,4-triazol-1yl)-3-{4-[1-(4-trifluoromethylbenzyl)-1H-1,2,4-triazol-3-yl]piperazin-1-y}butan-2-ol:

The title compound was prepared from the epoxide IV and triazolylpiperazine XIII (Ar=4-(trifluoromethyl)phenyl) by following the similar procedure described for example 21. After usual workup and column purification the title compound was obtained as a colorless solid in 18% yield.
m.p.: 69–72° C.
$^1$H NMR (CDCl$_3$) δ: 0.96 (d, 3H, CH$_3$), 2.49–2.54 (m, 2H, CH$_2$), 2.88–2.99 (m, 3H, CH$_2$ and CH ), 3.43 (m, 4H, 2XCH$_2$), 4.93 (AB q, 2H, CH$_2$), 4.98 (2 s merged, 3H, CH$_2$ and OH), 6.69–6.80 (m, 2H, Ar—H), 7.32–7.64 (m, 5H, Ar—H), 7.78 (2 s merged, 2H, Het-H), 7.98 (s, 1H, Het-H).
FAB-MS: 562.9 (MH$^+$), calcd. C$_{20}$H$_{27}$F$_5$N$_8$O 562.56.

Example 29

(2R,3R)-2-(2,4-Difluorophenyl)-3-(4-phenylpiperazin-1-yl)-1-(1H-1,2,4, triazol-1-yl)butan-2-ol:

The title compound was prepared by opening of the epoxide IV with 1-phenylpiperazine in the presence of lithium perchlorate by following similar procedure described to example 21. After column purification the compound was obtained as a colorless solid.
m.p.: 103–105° C.
1H NMR (CDCl$_3$) δ: 0.99 (d, 3H, CH$_3$), 2.6 (m, 2H, CH$_2$), 2.9–3.05 (m, 3H, CH$_2$ and CH), 4.89 (AB q, 2H, CH$_2$), 5.23 (s, 1H, OH), 6.7–7.0 (complex, 5H, Ar—H), 7.2–7.3 (m, 2H, Ar—H), 7.5 (m, 1H, Ar—H), 7.79 (s, 1H, Ar—H), 7.79 (s, 1H, Het-H), 7.97 (s, 1H, Het-H).
FAB-MS: 414.1 (MH$^+$), calcd. C$_{22}$H$_{25}$F$_2$N$_5$O 413.47.

Example 30

(2R,3R)-2-(2,4-Difluorophenyl)-3-[4-(4-nitrophenyl)piperazin-1-yl]1-(1H-1,2,4, triazol-1-yl)butan-2-ol:

The title compound was prepared similarly to example 21 using the oxirane IV(600 mg, 2.4 mmol), 4-nitrophenylpiperazine (660 mg, 3.2 mmol) and lithium perchlorate (383 mg, 3.6 mmol) as starting materials. After usual workup, the crude reaction product was purified on a column of silica gel (EtOAc/hexane) to give the desired compound as light yellow solid (920 mg, 84%).
m.p. 148–150° C.
$^1$H NMR (CDCl$_3$) δ: 0.94 (d, 3H, CH$_3$), 2.58–2.64 (m, 2H,), 3.06–3.13 (m, 3H), 3.4–3.5 (m, 4H), 4.93 (AB q, 2H, CH$_2$), 5.04 (s, 1H, OH), 6.7–6.85 (m and d merged, 4H, Ar—H), 7.38–7.51 (m, 1H, Ar—H), 7.79 (s, 1H, Het-H), 7.91 (s, 1H, Het-H), 8.13 (d, 2H, Ar—H).
FAB-MS: 459.2 (MH$^+$), calcd. C$_{22}$H$_{24}$F$_2$N$_6$O$_3$ 458.47

Example 31

(2R,3R)-3-[4-(4-Aminophenyl)piperazin-1-yl]2-(2,4-difluorophenyl)-1-(1H-1,2,4, triazol-1-yl)butan-2-ol:

To a solution of nitrocompound 30 (600 mg, 1.3 mmol) in 50 ml of ethyl acetate, 120 mg of 5% platinum on charcoal was added. The reaction mixture was hydrogenated in Parr hydrogenator at room temperature and 45 psi pressure for 18 h. The catalyst was removed by filtration and the filtrate was concentrated in vacuo. The pure amino compound 31 was obtained by dissolving the product in ethyl acetate and precipitating by addition of hexane (530 mg, 95%).
m.p.: 150–151° C.
$^1$H NMR (CDCl$_3$) δ: 0.98 (d, 3H, CH$_3$), 2.53–2.59 (m, 2H, CH$_2$), 2.89–3.04 (complex, 7H, 3XCH$_2$ and CH), 4.87 (AB q, 2H, CH$_2$), 6.6–6.9 (2d and m merged, 6H, Ar—H), 7.43–7.55 (m, 1H, Ar—H), 7.79 (s, 1H, Het-H), 7.98 (s, 1H, Het-H).
FAB-MS: 429.2 (MH$^+$), calcd. C$_{22}$H$_{26}$F$_2$N$_6$O 428.487.

Example 32

(2R,3R)-2-(2,4-Difluorophenyl)-3-[4-(4-ethoxycarbonylaminophenyl)piperazin-1-yl]-1-(1H-1,2,4-triazol-1-yl)butan-2-ol:

To a cooled (0° C.) mixture of amine 31 (300 mg, 0.7 mmol) and triethylamine (0.4 ml) in dichloromethane (30 ml) was added ethyl chloroformate (160 mg, 1.5 mmol) in dichloromethane (5 ml). The reaction mixture was stirred at 0° C. for 2 h, then diluted with 30 ml of chloroform, washed with water, brine and dried over sodium sulphate. The solvent was removed under reduced pressure, the residue was purified on a column of silica gel (hexane/EtOAc, 1:1 and 1:2) to give the title compound as amorphous solid (330 mg, 94%).
m.p. 90–92° C.
$^1$H NMR (CDCl$_3$)δ: 0.99 (d, 3H, CH$_3$), 1.29 (t, 3H, CH$_3$, J=7 Hz), 2.58 (m, 2H, CH$_2$), 2.95 (m, 3H, CH$_2$ and CH), 4.2 (q, 2H, CH$_2$, J=7 Hz), 4.88 (AB q, 2H, CH$_2$), 5.21 (s, 1H, OH), 6.44 (s, 1H, NH), 6.7–6.85 (m, 2H, Ar—H), 6.87 (d, 2H, Ar—H, J=8.9 Hz), 7.26 (d, 2H, Ar—H, J=8.9 Hz), 7.41–7.54 (m, 1H, Ar—H), 7.78 (s, 1H, Het-H), 7.97 (s, 1H, Het-H).
FAB-MS: 501.0 (MH$^+$), calcd. C$_{25}$H$_{30}$F$_2$N$_6$O$_3$ 500.55.

Example 33

(2R,3R)-2-(2,4-Difluorophenyl)-3-[4-(4-phenoxycarbonylaminophenyl)piperazin-1-yl]1-(1H-1,2,4,triazol-1-yl)butan-2-ol:

The title compound was prepared similarly to the above procedure using the amine 31(428 mg, 1 mmol) and phenyl chloroformate (235 mg, 1.5 mmol) in the presence of triethylamine (0.4 ml). After usual workup and purification on a silica gel column, the product was obtained as a colorless solid (475 mg, 89%).
m.p.: 95–97° C.
$^1$H NMR (CDCl$_3$) δ: 0.98 (d, 3H, CH$_3$), 2.58 (m, 2H, CH$_2$), 2.98 (m, 3H, CH$_2$ and CH), 3.15 (m, 4H, 2XCH$_2$), 4.88 (AB q, 2H, CH$_2$), 5.19 (s, 1H, OH), 6.7–7.0 (d and m merged, 4H, Ar—H), 7.2–7.6 (complex, 8H, Ar—H), 7.78 (s, 1H, Het-H), 7.96 (s, 1H, Het-H).
FAB-MS: 549.3 (MH$^+$), calcd. C$_{29}$H$_{30}$F$_2$N$_6$O$_3$ 548.594.

Example 34

(2R,3R)-2-(2,4-Difluorophenyl)-3-{4-[4-(semicarbazid-4-yl)phenyl]piperazin-1-yl)-1-(1H-1,2,4, triazol-1-yl)butan-2-ol:

To a solution of compound 33 (400 mg, 0.73 mmol) in dimethoxyethane (10 ml) was added hydrazine (1 ml) dropwise at room temperature and stirred for 4 h. The reaction mixture was concentrated under reduced pressure and the residue was treated with crushed ice. The precipitated product was isolated by filtration and washed with water and hexane to give the title compound as a colorless solid (300 mg, 85%).
m.p.: 180–182° C.
$^1$H NMR (CDCl$_3$) δ: 0.99 (d, 3H, CH$_3$), 2.54–2.60 (m, 2H, CH$_2$), 2.90–3.0 (m, 3H, CH$_2$ and CH), 3.10 (m, 4H, 2XCH$_2$), 3.8 (br s, 2H, NH2), 4.88 (AB q, 2H, CH$_2$), 5.7 (br s, 1H, OH), 6.09 s, 1H, NH), 6.7–6.9 (d and m merged, 4H, Ar—H), 7.3–7.6 (d and m merged, 3H, Ar—H), 7.8 (s, 1H, Het-H), 7.93 (br s, 1H, NH), 8.0 (s, 1H, Het-H).
FAB-MS: 487.0 (MH$^+$), calcd. C$_{23}$H$_{28}$F$_2$N$_8$O$_2$ 486.527.

Example 35

(2R,3R)-2-(2,4-Difluorophenyl)-1-(1H-1,2,4-triazol-1-yl)-3-{4-[4-(2H-1,2,4-triazol-3-one-4-yl)phenyl]piperazin-1-yl}butan-2-ol.

To a mixture of semicarbazide 34 (486 mg, 1 mmol) and formamidine acetate (416 mg, 4 mmol) in methoxyethanol (5 ml), triethylamine (0.8 ml) was added. The reaction mixture was heated at 110° C. for 18 h. Solvent was removed under reduced pressure and the residue was treated with crushed ice, extracted with ethyl acetate (3×30 ml). The combined extract was successively washed with water and brine and dried over sodium sulphate. The solvent was removed under reduced pressure, the crude product was purified on a column of silica gel (EtOAc/MeOH, 9:1) to give the triazolone 35 as a crystaline solid (320 mg, 65%).
m.p.: 223–225° C.
$^1$H NMR (CDCl$_3$) δ: 0.98 (d, 3H, CH$_3$, J=6.4 Hz), 2.57–2.63 (m, 2H, CH$_2$), 2.95–3.1 (m, 3H, CH$_2$ and CH), 4.9 (AB q, 2H, CH$_2$), 5.14 (s, 1H, OH), 6.7–6.82 (m, 2H, Ar—H), 6.98 (d, 2H, Ar—H, J=8.9 Hz), 7.37 (d, 2H, J=8.9, Ar—H), 7.4–7.5 (m, 1H, Ar—H), 7.62 (s, 1H, Het-H), 7.79 (s, 1H, Het-H), 7.95 (s, 1H, Het-H).
FAB-MS: 497.0 (MH$^+$), calcd. C$_{24}$H$_{26}$F$_2$N$_8$O$_2$ 496.522

Example 36

(2R,3R)-2-(2,4-Difluorophenyl)-3-[4-{4-[2-(3-pentyl)-2H-1,2,4-triazol-3-one-4-yl]phenyl]}piperazin-1-yl]-1-(1H-1,2, 4-triazol-1-yl)butan-2-ol.

To a mixture of triazolone 35 (248 mg, 0.5 mmol) and cesium carbonate (326 mg, 1 mmol) in DMF, 3-bromopentane (226 mg, 1.5 mmol) was added. The reaction mixture was heated at 80° C. for 18 h and concentrated in vacuo. The residue was treated with crushed ice, extracted with ethyl acetate (3×30 ml). The combined extract was washed with brine, dried (Na$_2$SO$_4$) and the solvent was removed under rduced pressure. The resulting crude product was purified on a column of silica gel (hexane/EtOAc) to give the title compound 36 as a crystaline solid (240 mg, 85%).

The title compound was also prepared in an alternate method in a convergent approach according to Scheme-1. Thus a mixture of (2R,3S)-2-(2,4-difluorophenyl)-3-methyl-2-(1H-1,2,4-triazol-1-yl)methyloxirane IV, piperazino compound XXIII (R=3-pentyl) and lithium perchlorate were heated in acetonitrile for 48 h. After usual workup and chromatographic purification, the title compound was obtained in 75% yield.
m.p.: 143–145° C.
$^1$H NMR (CDCl$_3$)δ: 0.88 (t, 6H, 2XCH$_3$), 0.98 (d, 3H, CH$_3$), 1.65–1.8 (m, 4H, 2XCH$_2$), 2.60 (m, 2H, CH$_2$), 3.1 (m, 3H, CH$_2$ and CH), 3.2 (m, 4H, 2XCH$_2$), 4.12 (m, 1H, CH), 4.9 (AB q, 2H, CH$_2$), 5.18 (s, 1H, OH), 6.7–6.8 (m, 2H, Ar—H), 6.97 (d, 2H, Ar—H, J=9 Hz), 7.4–7.6 (d and m merged, 3H, Ar—H), 7.64 (s, 1H, Het-H), 7.79 (s, 1H, Het-H), 7.96 (s, 1H, Het-H).
FAB-MS: 567.3 (MH$^+$), calcd. C$_{29}$H$_{36}$F$_2$N$_8$O$_2$ 566.657.

Example 37

(2S,3R)-2-(2,4-Difluorophenyl)-3-[4-{4-[2-(3-pentyl)-2H-1,2,4-triazol-3-one-4-yl]phenyl}piperazin-1-yl]-1-(1H-1,2,4-triazol-1-yl)butan-2-ol.

The title compound was prepared from (2S, 3S)-2-(2,4-difluorophenyl)-3-methyl-2-(1H-1,2,4-triazol-1-yl) methyloxirane and piperazino compound XXIII (R=3-pentyl) by following the similar procedure described for the example 36.

Yield 70%, colorless solid.

m.p.: 83–85° C.

$^1$H NMR (CDCl$_3$) δ: 0.88 (t, 6H, 2XCH$_3$), 1.25 (d, 3H, CH$_3$), 1.65–1.84 (m, 4H, 2XCH$_2$), 2.46 (m, 2H, CH$_2$), 2.75 (m, 2H, CH$_2$), 2.93 (m, 4H, 2XCH$_2$), 3.19 (q, 1H, CH), 4.05 (m, 1H, CH), 4.44 (d, 1H, J=14 Hz), 4.95 (d, 1H, J=14 Hz), 4.98 (s, 1H, OH), 6.64–6.77 (m, 2H, Ar—H), 6.74 (d, 2H, Ar—H), 7.29–7.43 (m, 3H Ar—H), 7.59 (s, 1H, Het-H), 7.77 (s, 1H, Het-H), 7.93 (s, 1H, Het-H).

FAB-MS: 567.2 (MH$^+$), calcd. C$_{29}$H$_{36}$F$_2$N$_8$O$_2$ 566.657.

Example 38

(2S,3S)-2-(2,4-Difluorophenyl)-3-[4-{4-[2-(3-pentyl)-2H-1,2,4-triazol-3-one-4-yl]phenyl}piperazin-1-yl]-1-(1H-1,2,4-triazol-1-yl)butan-2-ol.

The title compound was prepared from (2S,3R)-2-(2,4-difluorophenyl)-3-methyl-2-(1H-1,2,4-triazol-1-yl) methyloxirane and piperazino compound XXIII (R=3-pentyl) by following the similar procedure described for the example 36.

Yield 87%, off-white solid.

m.p.: 218–220° C.

$^1$H NMR(CDCl$_3$) δ: 0.88 (t, 6H, 2XCH$_3$), 0.97 (d, 3H, CH$_3$), 1.70–1.84 (m, 4H, 2XCH$_2$), 2.63 (m, 2H, CH$_2$), 3.01 (m, 3H, CH$_2$ and CH), 3.22 (m, 4H, 2XCH$_2$), 4.12 (m, 1H, CH), 4.90 (AB q, 2H, CH$_2$), 5.14 (s, 1H, OH), 6.69–6.82 (m, 2H, Ar—H), 6.96 (d, 2H, Ar—H), 7.40–7.49 (m and d merged, 3H, Ar—H), 7.63 (s, 1H, Het-H), 7.79 (s, 1H, Het-H), 7.95 (s, 1H, Het-H).

FAB-MS: 567.4 (MH$^+$), calcd. C$_{29}$H$_{36}$F$_2$N$_8$O$_2$ 566.657.

Example 39

(2R,3 S)-2-(2,4-Difluorophenyl)-3-[4-(4-[2-(3-pentyl)-2H-1,2,4-triazol-3-one-4-yl]phenyl)piperazin-1-yl]1-(1H-1,2,4-triazol-1-yl)butan-2-ol.

The title compound was prepared from (2R,3R)-2-(2,4-difluorophenyl)-3-methyl-2-(1H-1,2,4-triazol-1-yl) methyloxirane and piperazino compound XXIII (R=3-pentyl) by following the similar procedure described for the example 36.

Yield 60%, colorless solid.

m.p.: 110–113° C.

$^1$H NMR (CDCl$_3$) δ: 0.87 (t, 6H, 2XCH$_3$), 1.25 (d, 3H, J=7 Hz), 1.69–1.87 (m, 4H, 2XCH$_2$), 2.46 (m, 2H, CH$_2$), 2.75–2.95 (m, 6H, 3XCH$_2$), 3.19 (q, 1H, J=7 Hz), 4.07 (m, 1H, CH), 4.45 (d, 1H, J=15 Hz), 4.94 (d, 1H, J=15 Hz), 5.03 (s, 1H, OH), 6.66–6.76 (m, 2H, Ar—H), 6.87 (d, 2H, Ar—H), 7.34–7.39 (d and m merged, 3H, Ar—H), 7.60 (s, 1H, Het-H), 7.77 (s, 1H, Het-H), 7.93 (s, 1H, Het-H).

FAB-MS: 567.1 (MH$^+$), calcd. C$_{29}$H$_{36}$F$_2$N$_8$O$_2$ 566.657.

Example 40

(2R,3R)-3-[4-{4-[2-(2-Butyl)-2H-1,2,4-triazol-3-one-4-yl]phenyl}piperazin-1-yl]2-(2,4-difluorophenyl)-1-(1H-1,2,4-triazol-1-yl)butan-2-ol.

The example 40 was prepared similarly to the above procedure by alkylation of triazolone 35 with 2-bromobutane in the presence of cesium carbonate. After column chromatography the product was obtained as a colorless solid.

Yield 88%.

m.p.: 156–157° C.

$^1$H NMR (CDCl$_3$) δ: 0.90 (t, 3H, CH$_3$), 0.98 (d, 3H, CH$_3$), 1.6–1.9 (m, 2H, CH$_2$), 2.60 (m, 2H, CH$_2$), 3.0 (m, 3H, CH$_2$ and CH), 3.22 (m, 4H, 2XCH$_2$), 4.29 (m, 1H, CH), 4.9 (AB q, 2H, CH$_2$), 5.14 (s, 1H, OH), 6.65–6.85 (m, 2H, Ar—H), 6.96 (d, 2H, Ar—H, J=8.9 Hz), 7.5 (m, 1H, Ar—H), 7.61 (s, 1H, Het-H), 7.79 (s, 1H, Het-H), 7.95 (s, 1H, Het-H).

FAB-MS: 553.1 (MH$^+$), calcd. C$_{28}$H$_{34}$F$_2$N$_8$O$_2$ 552.573.

Example 41

(2R,3R)-2-(2,4-Difluorophenyl)-3-[4-{4-[2-(2-propyl)-2H-1,2,4-triazol-3-one-4-yl]phenyl}piperazin-1-yl]-1-(1H-1,2,4-triazol-1-yl)butan-2-ol.

The title compound 41 was prepared by alkylation of triazolone 35 with 2-bromopropane in the presence of cesium carbonate following the procedure similar to the above described for example 36.

Yield 80%.

m.p.: 166–167° C.

$^1$H NMR (CDCl$_3$) δ: 0.97 (d, 3H, CH$_3$), 1.40 (d, 6H, 2XCH$_3$), 2.60 (m, 2H, CH$_2$), 3.0 (m, 3H, CH$_2$ and CH), 3.22 (m, 4H, 2XCH$_2$), 4.55 (m, 1H, CH), 4.9 (AB q, 2H, CH$_2$), 5.15 (s, 1H, OH), 6.7–6.85 (m, 2H, Ar—H), 6.96 (d, 2H, Ar—H, J=9 Hz), 7.38 (d, 2H, Ar—H, J=9 Hz), 7.5 (m, 1H, Ar—H), 7.59 (s, 1H, Het-H), 7.79 (s, 1H, Het-H), 7.95 (s, 1H, Het-H).

FAB-MS: 539 (MH$^+$), calcd. C$_{27}$H$_{32}$F$_2$N$_8$O$_2$ 538.6.

Example 42

(2R,3R)-2-(2,4-Difluorophenyl)-3-[4-{4-[2-(2-hydroxypropyl)-2H-1,2,4-triazol-3-one-4-yl]phenyl}piperazin-1-yl]-1-(1H-1,2,4-triazol-1-yl)butan-2-ol.

To a mixture of triazolone 35 (248 mg, 0.5 mmol) and potassium carbonate (138 mg, 1 mmol) in DMF (6 ml), 1,2-epoxypropane (870 mg, 15 mmol) was added. The reaction mixture was heated at 60° C. for 18 h and concentrated in vacuo. The residue was treated with crushed ice, extracted with ethyl acetate (3×30 ml). The combined extract was washed with brine, dried (Na$_2$SO$_4$) and the solvent was removed under reduced pressure. The resulting crude product was purified on a column of silica gel (EtOAc/MeOH, 9:1) to give the hydoxypropyltriazolone 42 as a colorless solid (200 mg, 72%).

m.p.: 110–112° C. (decomp).

$^1$H NMR (CDCl$_3$) δ: 0.97 (d, 3H, CH$_3$), 1.28 (d, 3H, CH$_3$), 2.60 (m, 2H, CH$_2$), 2.9–3.1 (m and q merged, 3H, CH$_2$ and CH), 3.23 (m, 4H, 2XCH$_2$), 3.7–4.0 (m, 2H, CH$_2$), 4.8–5.0 (AB q, 2H, CH$_2$), 5.12 (s, 1H, OH), 6.65–6.85 (m, 2H, Ar—H), 6.96 (d, 2H, Ar—H, J=9 Hz), 7.37 (d, 2H, Ar—H, J=9 Hz), 7.5 (m, 1H, Ar—H), 7.63 (s, 1H, Het-H), 7.78 (s, 1H, Het-H), 7.94 (s, 1H, Het-H).

FAB-MS: 555.3 (MH$^+$), calcd. C$_{27}$H$_{32}$F$_2$N$_8$O$_3$ 554.60 tert-Butyl 4-(4-nitrophenyl)piperazine-1-carboxylate (XVII: X=H):

To a solution of 1-(nitrophenyl)piperazine (20.7, 0.1 mol) and triethylamine (21 ml) in dichloromethane (250 ml) at 0–5° C. was added dropwise a solution of di-tert-butyldicarbonate in dichloromethane (50 ml). The resulting mixture was stirred at 0–5° C. for 2 h and at room temperature for 18 h. Then the reaction mixture was diluted with 100 ml of chloroform, washed with water, brine and dried over sodium sulphate. The solvent was removed under reduced pressure and the residue was triturated with hexane and hexane/ethyl acetate mixture to give the title compound as a yellow solid (29 g, 94%).

$^1$H NMR (CDCl$_3$) δ: 1.5 (s, 9H, 3XCH$_3$), 3.43 (t, 4H, 2XCH$_2$), 3.6 (t, 4H, 2XCH$_2$), 6.8 (d, 2H, Ar—H, J=9 Hz), 8.15 (d, 2H, Ar—H, J=9 Hz).

tert-Butyl 4-(4-Aminophenyl)piperazine-1-carboxylate (XVIII: X=H):

A solution of butyl 4-(4-nitrophenyl)piperazine (60 g, 0.195 mol) in ethyl acetate (800 ml) was hydrogenated in the presence of 10% palldium on charcoal (6.0) at room temperature and 45 psi pressure in the Parr hydrogenator for 18 h. The catalyst was removed by filtration and the filtrate was concentrated in vacuo to give the title compound as a offwhite solid (50 g, 93%).

$^1$H NMR (CDCl$_3$) δ: 1.49 (s, 9H, 3XCH$_3$), 3.0 (t, 4H, 2XCH$_2$), 3.4 (br s, 2H, NH$_2$), 3.5 (t, 4H, 2XCH$_2$), 6.65 (d, 2H, Ar—H), 6.85 (d, 2H, Ar—H).

tert-Butyl 4-(4-Phenoxycarbonylaminophenyl)piperazine-1-carboxylate (XIX: X=H):

To a solution of tert-butyl 4-(4-aminophenyl)piperazine-1-carboxylate (50 g, 0.18 mol) and triethylamine (39 ml, 0.27 mol) in dichloromethane (400 ml) was added dropwise a solution of phenyl chloroformate (36.65 g, 0.23 mol) in dichloromethane (100 ml) at 0° C. The resulting reaction mixture was stirred for 2 h at 0° C. and additional 3 h at room temperature. Then diluted with chloroform (100 ml), washed with water, brine and dried over sodium sulphate. The solvent was removed under reduced pressure, the crude product was purified on a column of silica gel (hexane/EtOAc, 1:1) to give the tiltle compound as colorless solid (60 g, 84%).

m.p.: 158–160° C.

$^1$H NMR (CDCl$_3$) δ: 1.48 (s, 9H, 3XCH$_3$), 3.0–3.2 (m, 4H, 2XCH$_2$), 3.6 (m, 4H, 2XCH$_2$), 6.8 (brs, 1H, NH), 6.92 (d, 2H, Ar—H), 7.1–7.5 (complex, 7H, Ar—H).

4-[4-(4-t-BOC-piperazin-1-yl)phenylsemicarbazide (XX: X=H).

To a solution of tert-butyl 4-(phenoxycarbonylaminophenyl)piperazine-1-carboxylate (36 g, 90 mmol) in dimethoxyethane (300 ml), anhydrous hrazine (40 g, 1.25 mol) was added. The resulting reaction mixture was stirred at room temperature for 3–5 h. Solvent was removed under reduced pressure and the residue was treated with crushed ice and left overnight at room temperature. The precipitated solid was collected, washed with water and hexane to give the title compound as a offwhite solid (25 g, 82%).

$^1$H NMR (CDCl$_3$) δ: 1.48 (s, 9H, 3XCH$_3$), 3.06 (t, 4H, 2XCH$_2$), 3.58 (t, 4H, 2XCH$_2$), 3.82 (s, 2H, NH2), 5.98 (s, 1H, NH), 6.89 (d, 2H, Ar—H, J=8.9 Hz), 7.36 (d, 2H, Ar—H, J=8.9 Hz), 7.95 (s, 1H, NH).

4[4-(4-t-BOC-Piperazin-1-yl)phenyl-2H-1,2,4-triazol-3-one (XXI; X=H):

A mixture of 4-[4-(4-t-BOC-piperazin-1-yl) phenylsemicarbazide (25 g, 75 mmol), formamidine acetate (31, 2 g, 300 mmol) and triethylamine (50.5 ml, 360 mmol) in methoxyethanol (250 ml) was heated at 110° C. for 18 h. The solvent was removed under reduced pressure, the residue was treated with crushed ice and extracted with ethyl acetate (3×250 ml). Combined extract was successively washed with water and brine and dried over sodium sulphate. The solvent was removed under reduced pressure and the product was purified on a column of silica gel to give the title compound as a colorless solid (16.7 g, 65%).

m.p.: 195–197° C.

$^1$H NMR (CDCl$_3$) δ: 1.48 (s, (H, 9H, 3XCH$_3$), 3.16 (t, 4H, 2XCH$_2$), 3.59 (t, 4H, 2XCH$_2$), 6.98 (d, Ar—H, J=9 Hz), 7.38 (d, 2H, Ar—H), 7.62 (s, 1H, Het-H), 9.7 (brs, 1H, NH).

2-(3-Pentyl)-4[4-(4-t-BOC-piperazin-1-yl)phenyl-2H-1,2,4-triazol-3-one (XXII: X=H. R=3-pentyl):

A mixture of 4[4-(4-t-BOC-piperazin-1-yl)phenyl-2H-1,2,4-triazol-3-one XXI (3.45 g, 10 mmol), 3-bromopentane (4.53 g) and potassium carbonate (2.76 g, 20 mmol) in DMF (30 ml) was heated at 80° C. for 18 h. The solvent was removed under reduced pressure, the residue was diluted with water, extracted with ethyl acetate (3×50 ml). The combined extract was washed with water, brine, dried (Na$_2$SO$_4$) and concentrated in vacuo. The resulting product was purified on a column of silica gel (2.9 g, 70%) to give the title compound as a colorless solid.

m.p.: 96–97° C.

$^1$H NMR (CDCl$_3$) δ: 0.88 (t, 6H, 2XCH$_3$), 1.48 (s, 9H, 3XCH$_3$), 1.7–1.9 (m, 4H, 2XCH$_2$), 3.15 (t, 4H, 2XCH$_2$), 3.59 (t, 4H, 2XCH$_2$), 4.05 (m, 1H, CH), 6.98 (d, 2H, Ar—H, J=9 Hz), 7.44 (d, 2H, Ar—H, J=9 Hz), 7.63 (s, 1H, Het-H).

2-(3-Pentyl)-4-[4-(piperazin-1-yl)phenyl]-2H-1,2,4-triazol-3-one (XXIII: X=H: R=3-pentyl):

To a solution of 2-(3-pentyl)-4-[4-(4-t-BOC-piperazin-1-yl)phenyl-1H-1,2,4-triazol-3-one (2.5 g, 6 mmol) in ethyl acetate (30 ml), 30 ml of 10% hydrochloric acid was added. The resulting heterogenious mixture was stirred at room temperature for 5 h. Solvent was removed under reduced pressure, the residue was diluted with water, basified with potassium carbonate and extracted with chloroform (3×50 ml). The combined extract was washed with water, brine, dried (Na$_2$SO$_4$) and concentrated to give the title compound as colorless solid (1.8 g, 95%).

m.p.: 135–137° C.

$^1$H NMR (CDCl$_3$) δ:0.88 (t, 6H, 2XCH$_3$), 1.7–1.9 (m, 4H, 2XCH$_2$), 3.07 (m, 4H, 2XCH$_2$), 3.18 (m, 4H, 2XCH$_2$), 4.05 (m, 1H, CH), 6.95 (d, 2H, Ar—H), 7.42 (d, 2H, Ar—H), 7.63 (s, 1H, Het-H).

2-(2-Butyl)-4[4-(4-t-BOC-piperazin-1-yl)phenyl]2H-1,2,4-triazol-3-one (XXII: X=H, R=2-butyl):

The title compound was obtained by alkylation of triazolone XXI with 2-bromobutane in the presence of potassium carbonate.

m.p.: 134–135° C.

$^1$H NMR (CDCl$_3$) δ: 0.90 (t, 3H, CH$_3$), 1.39 (d, 3H, CH$_3$), 1.48 (s, 9H, 3XCH$_3$), 1.8 (m, 2H, CH$_2$), 3.15 (t, 4H, 2XCH$_2$), 3.59 (t, 4H, 2XCH$_2$), 4.3 (m, 1H, CH), 6.97 (d, 2H, Ar—H, J=8.9 Hz), 7.42 (d, 2H, Ar—H, J=8.9 Hz), 7.61 (s, 1H, Het-H).

2-(2-Butyl)-4-[4-(piperazin-1-yl)phenyl]-2H-1,2,4-triazol-3-one (XXIII: X=H. R=2-butyl):

The title compound was obtained by removal of t-BOC group of 2-(2-butyl)-4[4-(4-t-BOC-piperazin-1-yl)phenyl]-2H-1,2,4-triazol-3-one with 3M hydrochloric acid.

m.p.: 91–93° C.

$^1$H NMR (CDCl$_3$) δ: 0.90 (t, 3H, CH$_3$), 1.39 (d, 3H, CH$_3$), 3.04 (m, 4H, 2XCH$_2$), 3.17 (m, 4H, 2XCH$_2$), 4.29 (m, 1H, CH), 6.98 (d, 2H, Ar—H, J=8.9 Hz), 7.4 (d, 2H, Ar—H, J=8.9 Hz), 7.61 (s, 1H, Het-H).

4-[4-(4-t-BOC-Piperazin-1-yl)phenyl]2-(2-propyl)-2H-1,2,4-triazol-3-one (XXII: X=H. R=2-propyl):

The title compound was obtained by alkylation of triazolone XXI with 2-bromopropane in the presence of potassium carbonate. m.p.: 166–167° C.

$^1$H NMR (CDCl$_3$) δ:1.41 (d, 6H, 2XCH$_3$), 1.49 (s, 9H, 3XCH$_3$), 3.16 (t, 4H, 2XCH$_2$), 3.59 (2XCH$_2$), 4.55 (m, 1H, CH), 6.97 (d, 2H, Ar—H, J=8.9 Hz), 7.40 (d, 2H, Ar—H, J=8.9 Hz), 7.59 (s, 1H, Het-H).

4-[4-(Piperazin-1-yl)phenyl]2-(2-propyl)-2H-1,2,4-triazol-3-one (XXIII; X=H, R=2-propyl): The title compound was obtained by removal of t-BOC group of 4-[4-(4-t-BOC-piperazin-1-yl)phenyl]-2-(2-propyl)-2H-1,2,4-triazol-3-one with 3M hydrochloric acid.

m.p.: 120–121° C.

¹H NMR (CDCl₃) δ: 1.41 (d, 6H, 2XCH₃), 3.04 (m, 4H, 2XCH₂), 3.17 (m, 4H, 2XCH₂), 4.55 (m, 1H, CH), 6.97 (d, 2H, Ar—H, J=9 Hz), 7.38 (d, 2H, Ar—H, J=9 Hz), 7.59 (s, 1H, Het-H).

2-(2-Hydroxypropyl)-4-[4-(4-t-BOC-piperazin-1-yl)phenyl]-2H-1,2,4-triazol-3-one (XXII: X=H. R=2-hydroxypropyl):

The title compound was obtained by alkylation of triazolone XXI with 1,2-epoxypropane in the presence of potassium carbonate.

m.p: 168–170° C.

¹H NMR (CDCl₃) δ: 1.28 (d, 3H, CH₃), 1.48 (s, 9H, 3XCH₃), 3.17 (t, 4H, 2XCH₂), 3.4 (brs, 1H, OH), 3.59 (t, 4H, 2XCH₂), 3.70 (dd, 1H), 3.96 (dd, 1H), 4.2 (m, 1H, CH), 6.98 (d, 2H, Ar—H, J=8.9 Hz), 7.39 (d, 2H, Ar—H, J=8.9 Hz), 7.63 (s, 1H, Het-H).

2-(2-Hydroxypropyl)-4-[4-(piperazin-1-yl)phenyl]-2H-1,2,4-triazol-3-one (XXIII: X=H. R=2-hydroxypropyl):

The title compound was obtained by removal of t-BOC group of 2-(2-hydroxypropyl)-4-[4-(4-t-BOC-piperazin-1-yl)phenyl]-2H-1,2,4-triazol-3-one with 3M hydrochloric acid.

¹H NMR (CDCl₃) δ: 1.28 (d, 3H, CH₃), 3.0 (m, 4H, 2XCH₂), 3.2 (m, 4H, 2XCH₂), 3.8–4.0 (m, 2H, CH₂), 4.2 (m, 1H, CH), 6.98 (d, 2H, Ar—H, J=9 Hz), 7.3 (d, 2H, Ar—H, J=9 Hz), 7.62 (s, 1H, Het-H)

Example 43

4-[4-(4-t-BOC-Piperazin-1-yl)phenyl]2-[(4-trifluoromethyl)benzyl]-2H-1,2,4-triazol-3-one (XXII: X=H. R=4-trifluoromethylbenzyl):

The title compound was prepared by alkylation of triazolone XXI (X=H) with 4-(trifluoromethyl)benzyl bromide in the presence of potassium carbonate. After usual workup and purification on a column of silica gel, the title compound was obtained in 95% yield as a colorless solid.

¹H NMR (CDCl₃) δ: 1.49 (s, 9H, 3xCH₃); 3.16 (t, 4H, 2x₂); 3.59 (t, 4H, 2x CH₂); 5.06 (s, 2H, CH₂); 6.98 (d, 2H, J=8.9 Hz, Ar—H), 7.39 (d, 2H, J=8.9 Hz, Ar—H); 7.5–7.60 (m, 6H, Ar—H); 7.64 (s, 1H, Het-H).

4-[4-(Piperazin-1-yl)phenyl]2-[(4-trifluoromethyl)benzyl]2H-1,2,4-triazol-3-one (XXIII: X=H. R=4-trifluoromethylbenzyl):

The title compound was obtained by removal of t-BOC group of 4-[4-(4-t-BOC-piperazin-1-yl)phenyl]-2-[(4-trifluoromethyl)benzyl]-2H-1,2,4-triazol-3-one with 3M hydrochloric acid. After usual workup the product was obtained as a colorless solid in 95% yield.

¹H NMR (DMSO-d₆) δ: 2.81–2.84 (m, 4H, 2xCH₂); 3.04–3.07 (m, 4H, 2x CH₂); 5.05 (s, 2H, CH₂); 7.0 (d, 2H, J=9 Hz, Ar—H); 7.43–7.53 (m, 4H, Ar—H); 7.73 (d, 2H, J=8 Hz, Ar—H); 8.38 (s, 1H, Het-H).

(2R,3R)-2-(2,4-Difluorophenyl) -1-(1H-1,2,4-triazol-1-yl)-3-[4-{4-[2-(4-trifluoromethylbenzyl)-2H-1,2,4-triazol-3-one-4-yl]phenyl}piperazin-1-yl]butan-2-ol (43):

The title compound was prepared from (2R,3S)-2-(2,4-difluorophenyl)-3-methyl-2-(1H-1,2,4-triazol-1-yl) methyloxirane IV and piperazino compound XXIII (R=4-trifluoromethylbenzyl; X=H) by following the similar procedure described for the example 36.

Colorless solid, 189–191° C., yield 65%.

¹H NMR (CDCl₃) δ: 0.98 (d, 3H, J=5.5 Hz, CH₃), 2.57–2.63 (m, 2H, CH₂); 3.0–3.05 (m, 3H); 3.08–3.23 (m, 4H, 2xCH₂); 4.814.99 (q, 2H, CH₂); 5.07 (s, 2H, CH₂); 5.15 (s, 1H); 6.68–7.64 (m, 12H); 7.79 (s, 1H, Het-H); 7.95 (s, 1H, Het-H).

FAB-MS: 657.3 (MH⁺); calcd. C₃₂H₃₁O₂F₅N₈ 656.64.

Example 44

4-[4-(4-tert-BOC-Piperazin-1-yl)phenyl]-2-(2,2,3,3-tetrafluoropropyl)-2H-1,2,4-triazol-3-one (XXII: X=H. R=2,2,3,3-tetrafluoropropyl):

The title compound was obtained by alkylation of triazolone XXI (X=H) with 2,2,3,3-tetrafluropropyl methanesulphonate in the presence of potassium carbonate. The product was obtained as light yellow solid in quantitative yield.

¹H NMR (CDCl₃) δ: 1.48 (s, 9H, 3xCH₃); 3.18 (t, 4H, 2xCH₂); 3.59 (t, 4H, 2xCH₂); 4.34–4.48 (m, 2H) 5.71–6.28 (m, 1H, CHF₂); 6.98 (d, 2H, Ar—H) 7.39 (d, 2H, Ar—H); 7.69 (s, 1H, Het-H).

4-[4-(Piperazin-1-yl)phenyl]-2-(2,2,3,3-tetrafluoropropyl)-2H-1,2,4-triazol-3-one (XXIII: X=H. R=2,2,3,3-tetrafluoropropyl):

The title compound was obtained by the deprotection of the BOC group of the above compound with 3N hydrochloric acid. The product was obtianed as light yellow solid in quantitative yield. This was used in the following step without further purification.

¹H NMR (CDCl₃) o: 3.01–3.21 (m, 8H); 4.334.62 (m, 3H, CH₂ and N—H); 5.67–6.29 (m, 1H, CHF₂); 6.97 (d, 2H, Ar—H); 7.37 (d, 2H, Ar—H); 7.70 (s, 1H, Het-H).

2R,3R)-2-(2,4-Difluorophenyl)-3-[4-{4-[2-(2,2,3,3-tetrafluoropropyl)-2H-1,2,4-triazol-3-one-4-yl]phenyl}piperazin-1-yl]-1-(1H-1,2,4-triazol-1 yl)butan-2-ol.

The title compound was prepared from (2R,3S)-2-(2,4-difluorophenyl)-3-methyl-2-(1H-1,2,4-triazol-1-yl) methyloxirane IV and piperazino compound XXIII (R=2,2,3,3,-tetrafluoropropyl; X=H) by following the similar procedure described for the example 36.

Colorless solid, Yield 55%.

m.p: 155–157° C.

¹H NMR (CDCl₃) δ: 0.97 (d, 3H, J=5.4 Hz, CH₃); 2.57–2.65 (m, 2H, CH₂); 3.00–3.23 (m, 7H); 4.35–4.48 (m, 2H, CH₂); 4.82–5.00 (m, 2H, CH₂); 5.13 (s, 1H); 5.71–6.28 (m, 1H, —CHF₂); 6.69–6.83 (m, 2H, Ar—H); 6.96 (d, 2H, J=9 Hz; Ar—H); 7.35–7.53 (m, 3H, Ar—H); 7.68 (s, 1H, Het-H); 7.79 (s, 1H, Het-H); 7.95 (s, 1H, Het-H).

FAB-MS: 611, 2 (MH⁺), calcd. C₂₇H₂₈O₂F₆N₈ 610.56.

Example 45

4-[4-(4-t-BOC-Piperazin-1-yl)phenyl]2-(2,2,2-trifluoroethyl)-2H-1,2,4-triazol-3-one (XXII: X=H. R=2,2,2-trifluoroethyl):

The title compound was prepared from the reaction of triazolone XXI (X=H) with 2,2,2-trifluroethyl bromide in a sealed vessel in the presence of potassium carbonate. After usual workup and purification on a column of silica gel, the alkylated compound was obtained as a colorless solid in 21% yield.

¹H NMR (CDCl₃) δ: 1.49 (s, 9H, 3xCH₃); 3.18 (t, 4H, 2xCH₂); 3.59 (t, 4H, 2xCH₂); 4.44 (q, 2H, CH₂); 6.98 (d, 2H, J=7 Hz, Ar—H); 7.38 (d, 2H, J=7 Hz, Ar—H); 7.69 (s, 1H, Het-H).

4-[4-(Piperazin-1-yl)phenyl]-2-(2,2,2-trifluoroethyl)-2H-1,2,4-triazol-3-one (XXIII: X=H, R=2,2,2-trifluoroethyl):

The title compound was obtained by deprotection of BOC group of the above compound with 3M hydrochloric acid.

¹H NMR (CDCl₃) δ:1.73 (s, 1H, N-H); 3.00–3.20 (m, 8H, 4xCH₂); 4.44 (q, 2H, CH₂); 6.95–7.00 (m, 2H, Ar—H); 7.34–7.39 (m, 2H, Ar—H); 7.68 (s, 1H, Het-H).

(2R,3R)-2-(2,4-Difluorophenyl) -1-(1H-1,2,4-triazol-1-yl)-3-[4-{4-[2-(2,2,2—trifluoroethyl)-2H-1,2,4-triazol-3-one-4-yl]phenyl]}piperazin-1-yl]butan-2-ol.

The title compound was prepared from (2R,3S)-2-(2,4-difluorophenyl)-3-methyl-2-(1H-1,2,4-triazol-1-yl) methyloxirane IV and piperazino compound XXIII (R=2,2, 2-trifluoroethyl, X=H) by following the similar procedure described for the example 36.
Colorless solid, yield: 59%.
m.p: 95–97° C.
$^1$H NMR (CDCl$_3$) δ: 0.90 (d, 3H, J=6.3 Hz, CH$_3$); 2.50–2.56 (m, 2H, CH$_2$); 2.93–3.16 (m, 7H); 4.37 (q, 2H, CH$_2$); 4.83 (m, 2H, CH$_2$); 6.61–6.91 (m, 4H, Ar—H); 7.27–7.46 (m, 3H, Ar—H); 7.61 (s, 1H, Het-H); 7.71 (s, 1H, Het-H); 7.88 (s, 1H, Het-H).
FAB-MS : 579.2 (MH$^+$), calcd. C$_{26}$H$_{27}$O$_2$F$_5$N$_8$ 578.55.

Example 46

2-(2,4-Difluorobenzyl)-4-[4-(4-tert-BOC-piperazin-1-yl)]-2H-1,2,4-triazol-3-one (XXII: X=H. R=2,4-difluorobenzyl):

The title compound was prepared by alkylation of triazolone XXI (X=H) with 2,4-difluorobenzyl bromide in the presence of potassium carbonate. After usual workup the product was obtained in quantitative yield as a colorless solid.
$^1$H NMR (CDCl$_3$) δ: 1.49 (3, 9H, 3xCH$_3$); 3.17 (t, 4H, 2xCH$_2$); 3.59 (t, 4H, 2xCH$_2$); 5.04 (s, 2H, CH$_2$); 6.78–7.01 (m, 4H, Ar—H); 7.29–7.45 (m, 3H, Ar—H); 7.63 (s, 1H, Het-H).
2-(2,4-Difluorobenzyl)-4-[4-(4-piperazin-1-yl)-2H-1,2,4-triazol-3-one (XXIII; X=H. R=2,4-difluorobenzyl): The title compound was obtained by deprotection of BOC group of the above compound with 3N hydrochloric acid.
Colorless solid, 70% yield.
$^1$H NMR$_3$) δ: 1.70 (s, 1H, N—H); 2.92–3.10 (m, 8H, 4xCH$_2$); 4.96 (s, 2H, CH$_2$); 6.71–6.91 (m, 4H, Ar—H); 7.21–7.37 (m, 3H, Ar—H); 7.54 (s, 1H, Het-H).
(2R,3R)-3-[4-{4-[2-(2,4-Difluorobenzyl)-2H-1,2,4-triazol-3-one-4-yl]phenyl]}piperazin-1-yl]-2-(2,4-difluorophenyl)-1-(1H-1,2,4-triazol-1-yl)butan-2-ol.

The title compound was prepared from (2R,3S)-2-(2,4-difluorophenyl)-3-methyl-2-(1H-1,2,4-triazol-1-yl) methyloxirane and piperazino compound XXIII (R=2,4-difluorobenzyl, X=H) by following the similar procedure described for the example 36.
Colorless solid, yield 53%
m.p.: 161–163° C.
$^1$H NMR (CDCl$_3$) δ: 0.91 (d, 3H, J=5.6 Hz, CH$_3$); 2.49–2.57 (m, 2H, CH$_2$); 2.91–3.14 (m, 7H); 4.73–4.91 (m, 2H, CH$_2$); 4.97 (s, 2H, CH$_2$); 5.09 (s, 1H); 6.60–6.90 (m, 6H, Ar—H); 7.25–7.45 (m, 4H, Ar—H); 7.54 (s, 1H, Het-H); 7.70 (s, 1H, Het-H); 7.87 (s, 1H, Het-H).
FAB-MS: 623.1 (MH$^+$); calcd. C$_{30}$H$_{30}$ F$_4$O$_2$N$_8$ 622.63.

Example 47

4-[4-(4-tert-BOC-Piperazin-1-yl)phenyl-2-(4-trifluoromethoxy)benzyl-2H-1,2,4-triazol-3-one (XXII: X=H. R=4-trifluoromethoxybenzyl):

The title compound was prepared by alkylation of triazolone XXI (X=H) with 4-(trifluoromethoxy)benzyl bromide in the presence of potassium carbonate. After usual workup the product was obtained in 90% yield as a colorless solid.
$^1$H NMR (CDCl$_3$) δ:1.49 (s, 9H, 3xCH$_3$), 3.13–3.18 (m, 4H, 2xCH$_2$); 3.56–3.61 (m, 4H, 2xCH$_2$); 5.00 (s, 2H, CH$_2$); 6.94–6.99 (m, 2H, Ar—H); 7.17–7.22 (m, 2H, Ar—H) 7.38–7.47 (m, 4H, Ar—H); 7.63 (s, 1H, Het-H).
4-[4-(Piperazin-1-yl)phenyl-2-(4-trifluoromethoxy)benzyl-2H-1,2,4-triazol-3-one (XXIII: X=H. R=4-trifluoromethoxybenzyl):

The title compound was obtained by removal of t-BOC group of the aboove compound with 3M hydrochloric acid.
Colorless solid, quantitative yield.
$^1$H NMR (CDCl$_3$) δ:1.64 (s, 1H, N—H); 3.01–3.20 (m, 8H, 4xCH$_2$); 5.01 (s, 2H, CH$_2$); 6.95–6.99 (m, 2H, Ar—H); 7.18–7.22 (m, 2H, Ar—H), 7.34–7.47 (m, 4H, Ar—H); 7.61 (s, 1H, Het-H).
(2R,3R)-2-(2,4-Difluorophenyl)-3-[4-{4-[2-(4-trifluoromethoxybenzyl)-2H-1,2,4-triazol-3-one-4-yl] phenyl}piperazin-1-yl]-1-(1H-1,2,4-triazol-1-yl)butan-2-ol:

The title compound was prepared from (2R,3S)-2-(2,4-difluorophenyl)-3-methyl-2-(1H-1,2,4-triazol-1-yl) methyloxirane and piperazino compound XXIII [R=4-(trifluoromethoxy)benzyl; X=H] by following the similar procedure described for the example 36.
Colorless solid, 91% yield
m.p.: 175–177° C.
$^1$H NMR (CDCl$_3$) δ: 0.98 (d, 3H, J=5.7 Hz, CH$_3$); 2.57–2.65 (m, 2H, CH$_2$); 2.99–3.22 (m, 7H); 4.82–4.92 (m, 2H, CH$_2$) 5.01 (s, 2H, CH$_2$); 5.15 (s, 1H); 6.68–7.54 (m, 11H, Ar—H); 7.62 (s, 1H, Het-H); 7.79 (s, 1H, Het-H); 7.95 (s, 1H, Het-H).
FAB-MS: 671.3 (MH$^+$), calcd. C$_{32}$H$_{31}$O$_3$F$_5$N$_8$ 670.64.

Example 48

2-(4-Methoxybenzyl)-4-[4-(4-tert-BOC-piperazin-1-yl) phenyl-2H-1,2,4-triazol-3-one (XXII: X=H. R=4-methoxybenzyl):

The title compound was prepared by alkylation of triazolone XXI (X=H) with 4-methoxybenzyl bromide in DMF in the presence of potassium carbonate.
Colorless solid, 96% yield.
$^1$H NMR (CDCl$_3$) δ: 1.49 (s, 9H, 3xCH$_3$); 3.12–3.17 (m, 4H, 2xCH$_2$); 3.55–3.61 (m, 4H, 2xCH$_2$); 3.77 (s, 3H, OCH$_3$); 4.94 (s, 2H, CH$_2$); 6.83–6.99 (m, 4H, Ar—H); 7.32–7.41 (m, 4H, Ar—H); 7.59 (s, 1H, Het-H).
2-(4-Methoxybenzyl)-4-[4-(piperazin-1-yl)phenyl-2H-1,2, 4-triazol-3-one (XXIII: X=H. R=4-methoxybenzyl):

The title compound was obtained by deprotection of t-BOC group of 2-(4-methoxybenzyl)-4-[4-(4-tert-BOC-piperazin-1-yl)phenyl-2H-1,2,4-triazol-3-one with 3M hydrochloric acid.
Colorless solid, 94% yield.
$^1$H NMR (CDCl$_3$) δ: 1.62 (s, 1H, N-H); 3.01–3.19 (m, 8H, 4xCH$_2$); 3.79 (s, 3H, OCH$_3$); 4.95 (s, 2H, CH$_2$); 6.86–6.99 (m, 4H, Ar—H); 7.35–7.39 (m, 4H, Ar—H); 7.57 (s, 1H, Het-H).
(2R,3R)-2-(2,4-Difluorophenyl)-3-[4-{4-[2-(4-methoxybenzyl)-2H-1,2,4-triazol-3-one-4-yl] phenyl}piperazin-1-yl]-1-(1H-1,2,4-triazol-1-yl)butan-2-ol:

The title compound was prepared from (2R,3S)-2-(2,4-difluorophenyl)-3-methyl-2-(1H-1,2,4-triazol-1-yl) methyloxirane IV and piperazino compound XXIII (R=4-methoxybenzyl; X=H) by following the similar procedure described for the example 36.
Colorless solid, yield 69%.
m.p. 178–179° C.
$^1$H NMR (CDCl$_3$) δ: 0.96 (d, 3H, J=6.8 Hz, CH$_3$); 2.56–2.62 (m, 2H CH$_2$); 2.99–3.21 (m, 7H); 3.79 (s, 3H, OCH$_3$); 4.89–4.99 (m, 2H, 2); 4.95 (s, 2H, CH$_2$); 5.14 (s, 1H); 6.68–6.97 (m, 6H, Ar—H); 7.35–7.53 (m, 5H, Ar—H), 7.58 (s, 1H, Het-H); 7.78 (s, 1H, Het-H); 7.95 (s, 1H, Het-H).
FAB-MS: 617.0 (MH$^+$), calcd. C$_{32}$H$_{34}$O$_3$F$_2$N$_8$ 616.67.

Example 49

2-(2,4-Bis-trifluoromethyl)benzyl-4-[4-(4-tert-BOC-piperazin-1-yl)phenyl]-2H-1,2,4-triazol-3-one (XXII: X=H. R=2,4-bis-trifluoromethylbenzyl):

The title compound was prepared by alkylation of triazolone XXI (X=H) with 2,4-bis(trifluoromethyl)benzyl bromide in the presence of potassium carbonate. After usual workup the product was obtained in 76% yield as a colorless solid.

$^1$H NMR (CDCl$_3$) δ: 1.49 (s, 9H, 3xCH$_3$); 3.15–3.20 (m, 4H, 2xCH$_2$); 3.57–3.63 (m, 4H, 2xCH$_2$); 5.31 (s, 2H, CH$_2$); 6.98–7.02 (m, 2H, Ar—H); 7.40–7.53 (m, 3H, Ar—H); 7.72 (s, 1H, Het-H); 7.77–7.95 (m, 2H, Ar—H).

2-(2,4-Bis-trifluoromethyl)benzyl-4-[4-(piperazin-1-yl)phenyl]2H-1,2,4-triazol-3-one (XXIII; X=H. R=2,4-bis-trifluoromethylbenzyl):

The title compound was obtained by deprotection of t-BOC group of 4[-4-(4-tert-BOC-piperazin-1-yl)phenyl]-2-(2,4-bis-trifluoromethyl)benzyl-2H-1,2,4-triazol-3-one with 3M hydrochloric acid.

Colorless solid, 91% yield.

$^1$H NMR (CDCl$_3$) δ: 1.88 (s, 1H, NH); 3.02–3.21 (m, 8H, 4xCH$_2$); 5.31 (s, 2H, CH$_2$); 6.96–7.01 (m, 2H, Ar—H); 7.39–7.95 (m, 5H, Ar—H); 7.70 (s, 1H, Het-H).

(2R,3R)-3-[4-{4-[2-(2,4-Bis-trifluoromethylbenzyl)-2H-1,2,4-triazol-3-one-4-yl]phenyl}piperazin-1-yl]-2-(2,4-difluorophenyl)-1-(1H-1,2,4-triazol-1-yl)-butan-2-ol:

The title compound was prepared from (2R,3S)-2-(2,4-difluorophenyl)-3-methyl-2-(1H-1,2,4-triazol-1-yl) methyloxirane IV and piperazino compound XXIII [R=2,4-bis(trifluromethyl)benzyl; X=H] by following the similar procedure described for the example 36.

Colorless solid, yield: 70%.

m.p.: 146–148° C.

$^1$H NMR (CDCl$_3$) δ: 0.99 (d, 3H, J=6.8 Hz, CH$_3$); 2.58–2.66 (m, 2H, CH$_2$); 3.01–3.24 (m, 7H); 4.82–5.00 (m, 2H, CH$_2$); 5.14 (s, 1H); 5.31 (s, 2H, CH$_2$); 6.69–6.83 (m, 2H, Ar—H); 6.96–7.00 (m, 2H, Ar—H) 7.40–7.53 (m, 4H, Ar—H); 7.72 (s, 1H, Het-H) 7.77–7.81 (m, 2H, Ar—H & Het-H); 7.95 (s, 2H, Ar—H & Het-H).

FAB-MS: 723 (MH$^+$), calcd. 722.64.

Example 50

4-[4-(4-tert-BOC-Piperazin-1-yl)phenyl]2-[4-(2,2,3,3-tetrafluoropropoxy)benzyl]-2H-1,2,4-triazol-3-one [XXII; X=H, R=4-(2,2,3,3-tetrafluoropropoxy)benzyl]:

The title compound was prepared by alkylation of triazolone XXI (X=H) with 4-(2,2,3,3-tetrafluoropropoxy) benzyl bromide in the presence of potassium carbonate. After usual workup the product was obtained in 81% yield as a colorless solid.

$^1$H NMR (CDCl$_3$) δ: 1.49 (s, 9H, 3XCH$_3$), 3.12–3.17 (m, 4H, 2XCH$_2$), 3.55–3.60 (m, 4H, 2XCH$_2$), 4.26–4.37 (m, 2H, OCH$_2$), 4.94 (s, 2H, CH$_2$), 5.76–6.36 (m, 1H, CF$_2$H), 6.86–6.98 (m, 4H, Ar—H), 7.37 (m, 4H, Ar—H), 7.60 (s, 1H, Het-H).

4-[4-(Piperazin-1-yl)phenyl]2-[4-(2,2,3,3-tetrafluoropropoxy)benzyl]-2H-1,2,4-triazol-3-one [XXIII: X=H, R=4-(2,2,3,3-tetrafluoropropoxy)benzyl]:

The title compound was obtained by deprotection of t-BOC group of the above compound with 3M hydrochloric acid. After usual workup the product was obtained in 98% yield as colorless solid.

$^1$H NMR (CDCl$_3$) δ: 1.87 (s, 1H, NH), 3.01–3.19 (m, 8H, 4XCH$_2$), 4.27–4.39 (m, 2H, OCH$_2$), 4.96 (s, 2H, CH$_2$), 5.77–6.35 (m, 1H, CF$_2$H), 6.89–6.99 (m, 4H, Ar—H), 7.33–7.42 (m, 4H, Ar—H), 7.58 (s, 1H, Het-H).

(2R,3R)-2-(2,4-Difluorophenyl)-3-[4-(4-[2-((4-(2,2,3,3-tetrafluoropropoxy)benzyl))-2H-1,2,4-triazol-3-one-4-yl] phenyl)piperazin-1-yl]1-(1H-1,2,4-triazol-1-yl)butan-2-ol:

The title compound was prepared from (2R,3S)-2-(2,4-difluorophenyl)-3-methyl-2-(1H-1,2,4-triazol-1-yl) methyloxirane IV and piperazino compound XXIII [R=4-(2,2,3,3-tetrafluoropropoxy)benzyl; X=H] by following the similar procedure described for the example 36.

Yield 86%, colorless prisms.

m.p.: 83–85° C.

$^1$H NMR(CDCl$_3$) δ: 0.97 (d, 3H, CH$_3$), 2.57–2.62 (m, 2H, 2), 2.99–3.22 (m, 7H), 4.27–4.38 (m, 2H, CH$_2$), 4.81–4.99 (m, 2H, CH$_2$), 4.96 (s, 2H, CH$_2$), 5.15 (s, 1H, OH), 5.77–6.35 (m, 1H, CF$_2$H), 6.68–6.98 (m, 6H, Ar—H), 7.35–7.53 (m, 5H, Ar—H), 7.59 (s, 1H, Het-H), 7.78 (s, 1H, Het-H), 7.95 (s, 1H, Het-H).

FAB-MS: 717.3 (MH$^+$), calcd C$_{34}$H$_{34}$F$_6$O$_3$N$_8$ 716.69.

Example 51

4-[3-Fluoro-4-(4-tert-BOC-piperazin-1-yl)phenyl]-2-[4-(trifluoromethyl)benzyl]-2H-1,2,4-triazol-3-one (XXII: X=F, R=4-trifluoromethylbenzyl):

The title compound was prepared by alkylation of triazolone XXI (X=F) with (trifluoromethyl)benzyl bromide in the presence of potassium carbonate. After usual workup and purification on a column of silica gel, the title compound was obtained in 95% yield as a colorless solid.

$^1$H NMR (CDCl$_3$) δ: 1.48 (s, 9H, 3XCH$_3$), 3.04 (m, 4H, 2XCH$_2$), 3.60 (m, 4H, 2XCH$_2$), 5.06 (s, 2H, CH$_2$), 6.99 (m, 1H, Ar—H), 7.2–7.4 (m, 2H, Ar—H), 7.49–7.62 (m, 4H, Ar—H), 7.64 (s, 1H, Het-H).

4-[3-Fluoro-4-(piperazin-1-yl)phenyl]2-[4-(trifluoromethyl)benzyl]2H-1,2,4-triazol-3-one (XXIII: X=F, R=4-trifluoromethylbenzyl):

The title compound was obtained in 96% yield by deprotection of BOC group of the above compound with 3M hydrochloric acid.

$^1$H NMR (CDCl$_3$) δ: 3.0 (s, 8H, 4XCH$_2$), 5.05 (s, 2H, CH$_2$), 7.0 (m, 1H, Ar—H), 7.2–7.38 (m, 2H, Ar—H), 7.48–7.62 (m, 4H, Ar—H), 7.65 (s, 1H, Het-H).

(2R,3R)-2-(2,4-Difluorophenyl)-3-[4-{3-fluoro-4-[2-(4-trifluoromethyl)benzyl-2H-1,2,4-triazol-3-one-4-yl]phenyl) piperazin-1-yl]-1-(1H-1,2,4-triazol-1-yl)butan-2-ol:

The title compound was prepared from (2R,3S)-2-(2,4-difluorophenyl)-3-methyl-2-(1H-1,2,4-triazol-1-yl) methyloxirane IV and piperazino compound XXIII [R=4-(trifluoromethyl)benzyl; X=F] by following the similar procedure described for the example 36.

Colorless solid, Yield 69%.

m.p.: 189–191° C.

$^1$H NMR (CDCl$_3$) δ: 0.99 (d, 3H, CH$_3$), 2.65 (m, 2H, CH$_2$), 2.95–3.2 (m, 7H, 3XCH$_2$ and CH), 4.90 (AB q, 2H, CH$_2$), 5.07 (s, 2H, CH$_2$), 5.15 (s, 1H, OH), 6.7–6.85 (m, 2H, Ar—H), 7.04 (m, 1H, Ar—H), 7.2–7.62 (m, 7H, Ar—H), 7.64 (s, 1H, Het-H), 7.79 (s, 1H, Het-H), 7.95 (s, 1H, Het-H).

FAB-MS: 673.8 (MH$^+$), calcd. C$_{32}$H$_{30}$F$_6$N$_8$O$_2$ 672.634

We claim:
1. A compound of formula I, or an optical isomer or pharmaceutically acceptable salt thereof,

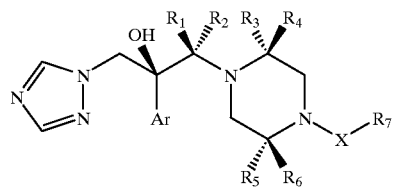

wherein:
Ar is a phenyl group which is unsubstituted or substituted by 1–3 substituents each independently selected from the group consisting of halogen, $CF_3$ and $OCF_3$;

$R_1$ and $R_2$ are each independently hydrogen or $C_1$–$C_4$ alkyl group which is unsubstituted or substituted by 1–3 substituents each independently selected from the group consisting of halogen, hydroxy, $C_1$–$C_4$ alkoxy and amino, with the proviso that where $R_1$ is hydrogen, $R_2$ is other than hydrogen, and vice versa;

$R_3$ and $R_4$ are each independently hydrogen or $C_1$–$C_4$ alkyl group which is unsubstituted or substituted by 1–3 substituents each independently selected from the group consisting of halogen, hydroxy, $C_1$–$C_4$ alkoxy and amino, or $R_3$ and $R_4$ together form =S;

$R_5$ and $R_6$ are each independently hydrogen or $C_1$–$C_4$ alkyl group which is unsubstituted or substituted by 1–3 substituents each independently selected from the group consisting of halogen, hydroxy, $C_1$–$C_4$ alkoxy and amino, or $R_5$ and $R_6$ together form =S;

X is a direct bond;
$R_7$ is a group of the formula

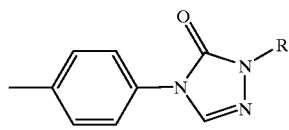

wherein
the phenyl is additionally unsubstituted or substituted with 1–2 additional substituents each independently selected from the group consisting of (1) $C_1$–$C_4$ alkyl which is unsubstituted or substituted with 1–3 substituents each independently selected from the group consisting of halogen, hydroxy, $C_1$–$C_4$ alkoxy and amino, (2) $C_1$–$C_4$ alkoxy, (3) halogen, (4) formyl, (5) carboxyl, (6) $C_1$–$C_4$ acyloxy, (7) $C_1$–$C_4$ alkoxycarbonylamino, (8) phenyl- or naphthyl-oxycarbonylamino, (9) semicarbazido, (10) formamido, (11) thioformamido, (12) hydroxy, (13) nitro, (14) amino, (15) furyl, (16) triazolyl, (17) thienyl, (18) oxazolyl, (19) imidazolyl and (20) triazolone-yl, and R is selected from the group consisting of (1) $C_1$–$C_{10}$ alkyl which is unsubstituted or substituted by 1–5 substituents each independently selected from the group consisting of halogen, hydroxy, $C_1$–$C_4$ alkoxy and amino, (2) phenyl which is unsubstituted or substituted with 1–3 substituents each independently selected from the group consisting of (a) $C_1$–$C_4$ alkyl which is unsubstituted or substituted with 1–3 substituents each independently selected from the group consisting of halogen, hydroxy, $C_1$–$C_4$ alkoxy and amino, (b) $C_1$–$C_4$ alkoxy, (c) halogen, (d) formyl, (e) carboxyl, (f) $C_1$–$C_4$ acyloxy, (g) $C_1$–$C_4$ alkoxycarbonylamino, (h) phenyl- or naphthyl-oxycarbonylamino, (i) semicarbazido, (j) formamido, (k) thioformamido, (l) hydroxy, (m) nitro, (n) amino, (o) furyl, (p) triazolyl, (q) thienyl, (r) oxazolyl, (s) imidazolyl, (t) triazolone-yl, (u) $CF_3$ and (v) $OCF_3$, (3) phenyl($C_1$–$C_4$ alkyl) which is unsubstituted or ring-substituted with 1–3 substituents each independently selected from the group consisting of (a) $C_1$–$C_5$ alkyl which is unsubstituted or substituted with 1–3 substituents each independently selected from the group consisting of halogen, hydroxy, $C_1$–$C_4$ alkoxy and amino, (b) halogen, (c) halo($C_1$–$C_4$ alkyl), (d) $C_1$–$C_4$ alkoxy, (e) hydroxy, (f) amino, (g) carboxyl, (h) trifluoromethoxy, (i) trifluoromethyl, (j) tetrafluoroethyl, (k) tetrafluoroethoxyl, (l) tetrafluoropropyl and (m) tetrafluoropropoxyl, (4) naphthyl($C_1$–$C_4$ alkyl) which may be substituted with 1–6 substituents selected from (a) $C_1$–$C_5$ alkyl which is unsubstituted or substituted with 1–3 substituents each independently selected from the group consisting of halogen, hydroxy, $C_1$–$C_4$ alkoxy and amino, (b) halogen, (c) ($C_1$–$C_4$ alkyl)halo, (d) $C_1$–$C_4$ alkoxy, (e) hydroxy, (f) amino, (g) carboxyl, (h) trifluoromethoxy, (i) trifluoromethyl, (j) tetrafluoroethyl, (k) tetrafluoroethoxyl, (l) tetrafluoropropyl and (m) tetrafluoropropoxyl, (5) methoxyl, (6) trifluoromethoxyl, (7) trifluoromethyl, (8) trifluoroethyl, (9) tetrafluoroethyl, (10) tetrafluoroethoxyl, (11) tetrafluoropropyl and (12) tetrafluoropropoxyl.

2. The compound according to claim 1, wherein Ar is selected from the group consisting of 4-fluorophenyl, 2-4-difluorophenyl, 2,4,6-trifluorophenyl, 4-chlorophenyl, 2,4-dichlorophenyl, 2,4,6-trichlorophenyl, 4-trifluoromethylphenyl and 4-trifluoromethoxyphenyl.

3. The compound according to claim 1, wherein Ar is a phenyl group having 1 to 2 substituents each independently selected from the group consisting of fluorine, chlorine, trifluoromethyl and trifluoromethoxy.

4. The compound according to claim 1, wherein Ar is selected from the group consisting of 2,4-d ifluorophenyl, 2 , 4-d ichlorophenyl, 4-trifluoromethylphenyl and 4-trifluoromethoxyphenyl.

5. The compound according to claim 1, wherein Ar is 2,4-difluorophenyl.

6. The compound according to claim 1, wherein $R_1$ is $C_1$–$C_4$ alkyl.

7. The compound according to claim 1, wherein $R_1$ is methyl.

8. The compound according to claim 1, wherein $R_2$ is hydrogen.

9. The compound according to claim 1, wherein $R_1$ and $R_2$ are the same, and the compound has a 2R isomeric configuration.

10. The compound according to claim 1, wherein $R_1$ and $R_2$ are different, and the compound has a 2R,3R isomeric configuration.

11. The compound according to claim 1, wherein Ar is 2,4-difluorophenyl, $R_1$ is methyl, and $R_2$ through $R_6$ are each hydrogen.

12. The compound according to claim 1, wherein $R_1$ is hydrogen and $R_2$ is methyl.

13. The compound according to claim 1, wherein $R_3$ through $R_6$ are each hydrogen.

14. The compound according to claim 1, wherein $R_3$ and $R_5$ are each methyl and $R_4$ and $R_6$ are each hydrogen.

15. The compound according to claim 1, wherein
R is selected from the group consisting of 2-propyl, 2-butyl, 3-pentyl, 2-hydroxypropyl, 4-trifluoromethylbenzyl, tetrafluoropropyl, trifluoroethyl, 2,4-difluorobenzyl, 4-methoxybenzyl, 4-trifluoromethoxybenzyl and 2,4-bis(trifluoromethyl) benzyl.

16. A compound wherein the compound is selected from the group consisting of:
- (2R,3R)-2-(2,4-Difluorophenyl)-3-[4-{4-[2-(3-pentyl)-2H-1,2,4-triazol-3-one-4-yl]phenyl}piperazin-1-yl]-1-(1H-1,2,4-triazol-1-yl)butan-2-ol,
- (2S, 3R)-2-(2,4-Difluorophenyl)-3-[4-{4-[2-(3-pentyl)-2H-1,2,4-triazol-3-one-4-yl]phenyl}piperazin-1-yl]-1-(1H-1,2,4-triazol-1-yl)butan-2-ol,
- (2S, 3S)-2-(2,4-Difluorophenyl)-3-[4-(4-[2-(3-pentyl)-2H-1,2,4-triazol-3-one-4-yl]phenyl}piperazin-1-yl]-1-(1H-1,2,4-triazol-1-yl)butan-2-ol,
- (2 R,3S)-2-(2,4-Difluorophenyl)-3-[4-{4-[2-(3-pentyl)-2H-1,2,4-triazol-3-one-4-yl]phenyl}piperazin-1-yl]-1-(1H-1,2,4-triazol-1-yl)butan-2-ol,
- (2R,3R)-3-[4-{4-[2-(2-Butyl)-2H-1,2,4-triazol-3-one-4-yl]phenyl}piperazin-1-yl]-2-(2,4-Difluorophenyl)-1-(1H-1,2,4-triazol-1-yl)butan-2-ol,
- (2R,3R)-2-(2,4-Difluorophenyl)-3-[4-{4-[2-(2-propyl)-2H-1,2,4-triazol-3-one-4-yl]phenyl}piperazin-1-yl]-1-(1H-1,2,4-triazol-1-yl)butan-2-ol,
- (2R,3R)-2-(2,4-Difluorophenyl)-3-[4-{4-[2-(2-hydroxypropyl)-2H-1,2,4-triazol-3-one-4-yl] phenyl}piperazin-1-yl]-1-(1H-1,2,4-triazol-1-yl)butan-2-ol, (2R,3R)-2-(2,4-Difluorophenyl)-1-(1H-1,2,4-triazol-1-yl)-3-[4-{4-[2-(4-trifluoromethyl)benzyl-2H-1,2,4-triazol-3-one-4-yl]phenyl}piperazin-1-yl]butan-2-ol,
- (2R,3R)-2-(2,4-Difluorophenyl)-3-[4-{4-[2-(2,2,3,3-tetrafluoro)propyl-2H-1,2,4-triazol-3-one4-yl] phenyl}piperazin-1-yl]-1-(1H-1,2,4-triazol-1-yl)-butan-2-ol,
- (2R,3R)-2-(2,4-Difluorophenyl)-1-(1H-1,2,4-triazol-1-yl)-3-[4-{4-[2-(2,2,2-trifluoro)ethyl-2H-1,2,4-triazol-3-one-4-yl]phenyl}piperazin-1-yl]butan-2-ol,
- (2R,3R)-3-[4-{4-[2-(2,4-Difluorobenzyl)-2H-1,2,4-triazol-3-one-4-yl]phenyl}piperazin-1-yl]-2-(2,4-Difluorophenyl)-1-(1H-1,2,4-triazol-1-yl)butan-2-ol,
- (2R,3R)-2-(2,4-Difluorophenyl)-3-[4-{4-[2-(4-trifluoromethoxy)benzyl-2H-1, 2,$^4$-triazol-3-one-4-yl] phenyl}piperazin-1-yl]-1-(1H-1,2,4-triazol-1-yl)-butan-2-ol,
- (2R,3R)-2-(2,4-Difluorophenyl)-3-[4-{4-[2-(4-methoxylbenzyl)-2H-1,2,4-triazol-3-one-4-yl] phenyl}piperazin-1-yl]-1-(1H-1,2,4-triazol-1-yl)-butan-2-ol,
- (2R, $^3$R)-$^3$-[$^4$-{4-[2-(2,4-Bis-trifluoromethylbenzyl)-2H-1,2,4-triazol-3-one-4-yl]phenyl}piperazin-1-yl]-2-(2, 4-difluorophenyl)-1-(1H-1 , 2,4-triazol-1-yl)-butan-2-ol,
- (2R,3R)-2-(2,4-Difluorophenyl)-3-[4-{4-[2-((4-(2,2,3,3-tetrafluoropropoxy)benzyl))-2H-1,2,4-triazol-3-one-4-yl]phenyl}piperazin-1-yl]-1-(1H-1,2,4-triazol-1-yl) butan-2-ol, and
- (2R,3R)-2-(2,4-Difluorophenyl)-3-[4-{3-fluoro-4-[2-(4-trifluoromethyl)benzyl-2H-1,2,4-triazol-3-one-4-yl] phenyl}piperazin-1-yl]-1-(1H-1,2,4-triazol-1-yl)butan-2-ol.

17. The compound according to claim 16, wherein the compound is selected from the group consisting of:
- (2R,3R)-2-(2,4-Difluorophenyl)-1-(1H-1,2,4-triazol-1-yl)-3-[4-{4-[2-(4-trifluoromethyl)benzyl-2H-1,2,4-triazol-3-one-4-yl]phenyl}piperazin-1-yl]butan-2-ol,
- (2R,3R)-2-(2,4-Difluorophenyl)-3-4-{4-[2-(4-trifluoromethoxy)benzyl-2H-1,2,4-triazol-3-one-4-yl] phenyl}piperazin-1-yl]-1-(1H-1,2,4-triazol-1-yl)-butan-2-ol,
- (2R,3R)-2-(2,4-Difluorophenyl)-3-[4-{4-[2-((4-(2,2,3,3-tetrafluoropropoxy)benzyl))-2H-1,2,4-triazol-3-one-4-yl]phenyl}piperazin-1-yl]-1-(1H-1,2,4-triazol-1-yl) butan-2-ol, and
- (2R,3R)-2-(2,4-Difluorophenyl)-3-[4-3-fluoro-4-2-(4-trifluoromethyl)benzyl-2H-1,2,4-triazol-3-one-4-yl] phenyl}piperazin-1-yl]-1-(1H-1,2,4-triazol-1-yl)butan-2-ol.

18. A pharmaceutical composition suitable for treating a fungal infection, comprising a pharmaceutically effective amount of the compound of claim 1 in combination with a pharmaceutically acceptable carrier or diluent.

19. The pharmaceutical composition according to claim 18, wherein the pharmaceutical composition is an oral formulation and the compound is present in an amount of 1 to 25% (w/w).

20. The pharmaceutical composition according to claim 18, wherein the pharmaceutical composition is an injectable formulation and the compound is present in an amount of 0.1 to 5% (w/w).

21. The pharmaceutical composition according to claim 18, wherein the pharmaceutical composition is a topical or rectal formulation and the compound is present in an amount of 1 to 10% (w/w).

22. A method of treating or preventing a fungal infection in a patient in need of such treatment or prevention, comprising administering to the patient a fungal infection treating- or preventing-amount of the compound of claim 1.

23. The method according to claim 22, wherein the compound is administered in a daily dose of 0.01 to 20 mg/kg patient.

24. The method according to claim 23, wherein the daily dose is divided into a plurality of individual doses.

25. The method according to claim 22, wherein the fungal infection is a topical infection.

26. The method according to claim 22, wherein the fungal infection is a systemic infection.

27. The method according to claim 22, wherein the fungal infection is a mucosal infection.

28. The method according to claim 22, wherein the fungal infection is a lung-invasive infection.

* * * * *